US012324645B2

(12) United States Patent
Fredrickson et al.

(10) Patent No.: US 12,324,645 B2
(45) Date of Patent: Jun. 10, 2025

(54) SYSTEMS AND METHODS FOR COLLISION AVOIDANCE USING OBJECT MODELS

(71) Applicant: Auris Health, Inc., Redwood City, CA (US)

(72) Inventors: Benjamin Robert Fredrickson, Belmont, CA (US); Nicholas J. Eyre, Redwood City, CA (US); Alexander Tarek Hassan, San Francisco, CA (US); Eloi Le Roux, San Francisco, CA (US)

(73) Assignee: Auris Health, Inc., Santa Clara, CA (US)

( * ) Notice: Subject to any disclaimer, the term of this patent is extended or adjusted under 35 U.S.C. 154(b) by 558 days.

(21) Appl. No.: 17/025,248

(22) Filed: Sep. 18, 2020

(65) Prior Publication Data

US 2021/0093407 A1    Apr. 1, 2021

Related U.S. Application Data

(60) Provisional application No. 62/906,613, filed on Sep. 26, 2019.

(51) Int. Cl.
*B25J 9/16*    (2006.01)
*A61B 34/00*   (2016.01)
(Continued)

(52) U.S. Cl.
CPC .............. *A61B 34/71* (2016.02); *A61B 34/37* (2016.02); *A61B 34/74* (2016.02); *B25J 9/02* (2013.01); *B25J 9/1676* (2013.01); *B25J 9/1694* (2013.01)

(58) Field of Classification Search
CPC ......... A61B 34/71; A61B 34/37; A61B 34/74; A61B 90/03; A61B 2017/00477;
(Continued)

(56) References Cited

U.S. PATENT DOCUMENTS 3,763,860 A   10/1973  Clarke
4,040,413 A    8/1977  Ohshiro
(Continued)

FOREIGN PATENT DOCUMENTS

CN   101443069 A   5/2009
CN   100515347 C   7/2009
(Continued)

OTHER PUBLICATIONS

International Preliminary Report on Patentability dated Apr. 7, 2022, issued in International Application No. PCT/IB2020/058717, 17 pages.
(Continued)

*Primary Examiner* — Abby Y Lin
*Assistant Examiner* — Danielle M Jackson
(74) *Attorney, Agent, or Firm* — Frost Brown Todd LLP

(57) ABSTRACT

Systems and methods for collision avoidance using object models are provided. In one aspect, a robotic medical system, includes a platform, one or more robotic arms coupled to the platform, a console configured to receive input commanding motion of the one or more robotic arms, a processor, and at least one computer-readable memory in communication with the processor. The processor is configured to control movement of the one or more robotic arms in a workspace based on the input received by the console, receive an indication of one or more objects are within reach of the one or more robotic arms, and update the model to include a representation of the one or more objects in the workspace.

30 Claims, 30 Drawing Sheets

(51) Int. Cl.
*A61B 34/37* (2016.01)
*B25J 9/02* (2006.01)

(58) Field of Classification Search
CPC ........ A61B 2034/102; A61B 2034/301; A61B 2090/064; B25J 9/02; B25J 9/1676; B25J 9/1694; B25J 9/1666; B25J 9/1682; G05B 2219/39082; G05B 2219/39091; G05B 2219/39096
See application file for complete search history.

(56) References Cited

U.S. PATENT DOCUMENTS

| | | | |
|---|---|---|---|
| 4,198,960 A | 4/1980 | Utsugi | |
| 4,470,407 A | 9/1984 | Hussein | |
| 4,532,935 A | 8/1985 | Wang et al. | |
| 4,685,458 A | 8/1987 | Leckrone | |
| 4,747,405 A | 5/1988 | Leckrone | |
| 4,854,301 A | 8/1989 | Nakajima | |
| 4,898,574 A | 2/1990 | Uchiyama | |
| 4,975,856 A | 12/1990 | Vold et al. | |
| 4,983,165 A | 1/1991 | Loiterman | |
| 5,029,574 A | 7/1991 | Shimamura et al. | |
| 5,085,659 A | 2/1992 | Rydell | |
| 5,150,452 A | 9/1992 | Pollack et al. | |
| 5,196,023 A | 3/1993 | Martin | |
| 5,199,417 A | 4/1993 | Muller et al. | |
| 5,217,465 A | 6/1993 | Steppe | |
| 5,308,323 A | 5/1994 | Sogawa et al. | |
| 5,318,589 A | 6/1994 | Lichtman | |
| 5,325,848 A | 7/1994 | Adams et al. | |
| 5,342,381 A | 8/1994 | Tidemand | |
| 5,344,395 A | 9/1994 | Whalen et al. | |
| 5,353,783 A | 10/1994 | Nakao et al. | |
| 5,370,609 A | 12/1994 | Drasler et al. | |
| 5,372,124 A | 12/1994 | Takayama et al. | |
| 5,411,016 A | 5/1995 | Kume et al. | |
| 5,431,649 A | 7/1995 | Muller et al. | |
| 5,441,485 A | 8/1995 | Peters | |
| 5,449,356 A | 9/1995 | Walbrink et al. | |
| 5,450,843 A | 9/1995 | Moll et al. | |
| 5,472,426 A | 12/1995 | Bonati et al. | |
| 5,496,267 A | 3/1996 | Drasler | |
| 5,501,667 A | 3/1996 | Verduin, Jr. | |
| 5,520,684 A | 5/1996 | Imran | |
| 5,545,170 A | 8/1996 | Hart | |
| 5,562,239 A | 10/1996 | Boiarski et al. | |
| 5,562,648 A | 10/1996 | Peterson | |
| 5,562,678 A | 10/1996 | Booker | |
| 5,572,999 A | 11/1996 | Funda et al. | |
| 5,573,535 A | 11/1996 | Viklund | |
| 5,613,973 A | 3/1997 | Jackson et al. | |
| 5,645,083 A | 7/1997 | Essig et al. | |
| 5,653,374 A | 8/1997 | Young et al. | |
| 5,658,311 A | 8/1997 | Baden | |
| 5,695,500 A | 12/1997 | Taylor et al. | |
| 5,697,949 A | 12/1997 | Giurtino et al. | |
| 5,710,870 A | 1/1998 | Ohm et al. | |
| 5,716,325 A | 2/1998 | Bonutti | |
| 5,737,500 A | 4/1998 | Seraji et al. | |
| 5,788,667 A | 8/1998 | Stoller | |
| 5,792,165 A | 8/1998 | Klieman | |
| 5,797,900 A | 8/1998 | Madhani et al. | |
| 5,798,627 A | 8/1998 | Gilliland et al. | |
| 5,810,770 A | 9/1998 | Chin et al. | |
| 5,876,325 A | 3/1999 | Mizuno et al. | |
| 5,893,869 A | 4/1999 | Barnhart et al. | |
| 5,897,491 A | 4/1999 | Kastenbauer et al. | |
| 5,924,175 A | 7/1999 | Lippitt et al. | |
| 5,943,056 A | 8/1999 | Sato et al. | |
| 5,989,230 A | 11/1999 | Frassica | |
| 6,071,281 A | 6/2000 | Burnside et al. | |
| 6,093,157 A | 7/2000 | Chandrasekaran | |
| 6,110,171 A | 8/2000 | Rydell | |
| 6,120,476 A | 9/2000 | Fung et al. | |
| 6,120,498 A | 9/2000 | Jani et al. | |
| 6,156,030 A | 12/2000 | Neev | |
| 6,174,318 B1 | 1/2001 | Bates et al. | |
| 6,183,435 B1 | 2/2001 | Bumbalough et al. | |
| 6,206,903 B1 | 3/2001 | Ramans | |
| 6,236,906 B1 | 5/2001 | Müller | |
| 6,322,557 B1 | 11/2001 | Nikolaevich et al. | |
| 6,375,635 B1 | 4/2002 | Moutafis et al. | |
| 6,394,998 B1 | 5/2002 | Wallace et al. | |
| 6,405,078 B1 | 6/2002 | Moaddeb et al. | |
| 6,440,061 B1 | 8/2002 | Wenner et al. | |
| 6,508,823 B1 | 1/2003 | Gonon | |
| 6,522,906 B1 | 2/2003 | Salisbury, Jr. et al. | |
| 6,577,891 B1 | 6/2003 | Jaross et al. | |
| 6,676,668 B2 | 1/2004 | Mercereau et al. | |
| 6,685,698 B2 | 2/2004 | Morley et al. | |
| 6,706,050 B1 | 3/2004 | Giannadakis | |
| 7,002,585 B1 | 2/2006 | Watanabe et al. | |
| 7,282,055 B2 | 10/2007 | Tsuruta | |
| 7,559,934 B2 | 7/2009 | Teague et al. | |
| 7,736,356 B2 | 6/2010 | Cooper et al. | |
| 7,963,911 B2 | 6/2011 | Turliuc | |
| 7,987,046 B1 | 7/2011 | Peterman et al. | |
| 8,002,713 B2 | 8/2011 | Heske et al. | |
| 8,004,229 B2 | 8/2011 | Nowlin et al. | |
| 8,021,326 B2 | 9/2011 | Moll et al. | |
| 8,038,598 B2 | 10/2011 | Khachi | |
| 8,092,397 B2 | 1/2012 | Wallace et al. | |
| 8,187,173 B2 | 5/2012 | Miyoshi | |
| 8,257,303 B2 | 9/2012 | Moll et al. | |
| 8,480,595 B2 | 7/2013 | Speeg et al. | |
| 8,523,762 B2 | 9/2013 | Miyamoto et al. | |
| 8,540,748 B2 | 9/2013 | Murphy et al. | |
| 8,541,970 B2 | 9/2013 | Nowlin et al. | |
| 8,652,030 B2 | 2/2014 | Matsuura et al. | |
| 8,749,190 B2 | 6/2014 | Nowlin et al. | |
| 8,786,241 B2 | 7/2014 | Nowlin et al. | |
| 8,820,603 B2 | 9/2014 | Shelton, IV et al. | |
| 8,821,480 B2 | 9/2014 | Burbank | |
| 8,882,660 B2 | 11/2014 | Phee et al. | |
| 8,945,163 B2 | 2/2015 | Voegele et al. | |
| 8,956,280 B2 | 2/2015 | Eversull et al. | |
| 9,179,979 B2 | 11/2015 | Jinno | |
| 9,259,282 B2 | 2/2016 | Azizian et al. | |
| 9,296,104 B2 | 3/2016 | Swarup et al. | |
| 9,345,456 B2 | 5/2016 | Tsonton et al. | |
| 9,345,544 B2 | 5/2016 | Hourtash et al. | |
| 9,375,284 B2 | 6/2016 | Hourtash | |
| 9,415,510 B2 | 8/2016 | Hourtash et al. | |
| 9,460,536 B2 | 10/2016 | Hasegawa et al. | |
| 9,480,534 B2 | 11/2016 | Bowling et al. | |
| 9,504,604 B2 | 11/2016 | Alvarez | |
| 9,510,911 B2 | 12/2016 | Hourtash | |
| 9,517,106 B2 | 12/2016 | Hourtash et al. | |
| 9,561,083 B2 | 2/2017 | Yu et al. | |
| 9,566,125 B2 | 2/2017 | Bowling et al. | |
| 9,592,042 B2 | 3/2017 | Titus | |
| 9,597,152 B2 | 3/2017 | Schaeffer et al. | |
| 9,622,827 B2 | 4/2017 | Yu et al. | |
| 9,636,184 B2 | 5/2017 | Lee et al. | |
| 9,668,768 B2 | 6/2017 | Piron et al. | |
| 9,675,422 B2 | 6/2017 | Hourtash et al. | |
| 9,687,310 B2 | 6/2017 | Nowlin et al. | |
| 9,713,509 B2 | 7/2017 | Schuh et al. | |
| 9,717,563 B2 | 8/2017 | Tognaccini et al. | |
| 9,727,963 B2 | 8/2017 | Mintz et al. | |
| 9,730,757 B2 | 8/2017 | Brudniok | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,782,229 B2 | 10/2017 | Crawford et al. | |
| 9,788,910 B2 | 10/2017 | Schuh | |
| 9,789,608 B2 | 10/2017 | Itkowitz et al. | |
| 9,844,412 B2 | 12/2017 | Bogusky et al. | |
| 9,867,635 B2 | 1/2018 | Alvarez et al. | |
| 9,918,681 B2 | 3/2018 | Wallace et al. | |
| 9,931,025 B1 | 4/2018 | Graetzel et al. | |
| 9,943,962 B2 | 4/2018 | Sattler et al. | |

(56) References Cited

U.S. PATENT DOCUMENTS

| | | |
|---|---|---|
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,029,367 B2 | 7/2018 | Hourtash |
| 10,071,479 B2 | 9/2018 | Swarup et al. |
| 10,080,576 B2 | 9/2018 | Romo et al. |
| 10,117,713 B2 | 11/2018 | Moctezuma De La Barrera et al. |
| 10,130,429 B1 | 11/2018 | Weir |
| 10,136,949 B2 | 11/2018 | Felder et al. |
| 10,136,959 B2 | 11/2018 | Mintz et al. |
| 10,145,747 B1 | 12/2018 | Lin et al. |
| 10,149,720 B2 | 12/2018 | Romo |
| 10,154,822 B2 | 12/2018 | Henderson et al. |
| 10,159,532 B1 | 12/2018 | Ummalaneni |
| 10,159,533 B2 | 12/2018 | Moll et al. |
| 10,169,875 B2 | 1/2019 | Mintz et al. |
| 10,219,868 B2 | 3/2019 | Weir |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,314,661 B2 | 6/2019 | Bowling et al. |
| 10,327,855 B2 | 6/2019 | Hourtash et al. |
| 10,350,017 B2 | 7/2019 | Bowling et al. |
| 10,350,390 B2 | 7/2019 | Moll et al. |
| 10,383,765 B2 | 8/2019 | Alvarez et al. |
| 10,398,518 B2 | 9/2019 | Yu et al. |
| 10,405,939 B2 | 9/2019 | Romo |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer et al. |
| 10,463,440 B2 | 11/2019 | Bowling et al. |
| 10,464,209 B2 | 11/2019 | Ho et al. |
| 10,470,830 B2 | 11/2019 | Hill et al. |
| 10,482,599 B2 | 11/2019 | Mintz et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan et al. |
| 10,539,478 B2 | 1/2020 | Lin et al. |
| 10,543,048 B2 | 1/2020 | Noonan et al. |
| 10,555,778 B2 | 2/2020 | Ummalaneni |
| 10,631,949 B2 | 4/2020 | Schuh et al. |
| 10,639,108 B2 | 5/2020 | Romo et al. |
| 10,639,109 B2 | 5/2020 | Bovay et al. |
| 10,639,114 B2 | 5/2020 | Schuh et al. |
| 10,646,291 B2 | 5/2020 | Turner |
| 10,667,871 B2 | 6/2020 | Romo et al. |
| 10,667,875 B2 | 6/2020 | DeFonzo et al. |
| 10,682,189 B2 | 6/2020 | Schuh et al. |
| 10,702,348 B2 | 7/2020 | Moll et al. |
| 10,716,461 B2 | 7/2020 | Jenkins |
| 10,743,751 B2 | 8/2020 | Landey et al. |
| 10,744,035 B2 | 8/2020 | Alvarez et al. |
| 10,751,140 B2 | 8/2020 | Wallace et al. |
| 10,765,303 B2 | 9/2020 | Graetzel et al. |
| 10,765,487 B2 | 9/2020 | Ho et al. |
| 10,779,898 B2 | 9/2020 | Hill et al. |
| 10,786,329 B2 | 9/2020 | Schuh et al. |
| 10,786,432 B2 | 10/2020 | Mintz et al. |
| 10,792,464 B2 | 10/2020 | Romo et al. |
| 10,792,466 B2 | 10/2020 | Landey et al. |
| 10,796,432 B2 | 10/2020 | Mintz et al. |
| 10,813,539 B2 | 10/2020 | Graetzel et al. |
| 10,814,101 B2 | 10/2020 | Jiang |
| 10,820,947 B2 | 11/2020 | Julian |
| 10,820,954 B2 | 11/2020 | Marsot et al. |
| 10,827,913 B2 | 11/2020 | Ummalaneni et al. |
| 10,828,118 B2 | 11/2020 | Schuh et al. |
| 10,835,153 B2 | 11/2020 | Rafii-Tari et al. |
| 10,850,013 B2 | 12/2020 | Hsu et al. |
| 10,959,792 B1 | 3/2021 | Huang et al. |
| 11,547,468 B2 | 1/2023 | Shelton, IV et al. |
| 11,638,999 B2 | 5/2023 | Itkowitz et al. |
| 11,701,187 B2 | 7/2023 | Huang et al. |
| 2002/0019644 A1 | 2/2002 | Hastings et al. |
| 2002/0082612 A1 | 6/2002 | Moll et al. |
| 2002/0111608 A1 | 8/2002 | Baerveldt et al. |
| 2002/0111621 A1 | 8/2002 | Wallace et al. |
| 2003/0004455 A1 | 1/2003 | Kadziauskas et al. |
| 2003/0040681 A1 | 2/2003 | Ng et al. |
| 2003/0065358 A1 | 4/2003 | Frecker et al. |
| 2003/0100892 A1 | 5/2003 | Morley et al. |
| 2003/0109780 A1 | 6/2003 | Coste-Maniere et al. |
| 2003/0109877 A1 | 6/2003 | Morley et al. |
| 2003/0109889 A1 | 6/2003 | Mercereau et al. |
| 2003/0158545 A1 | 8/2003 | Hovda et al. |
| 2003/0181809 A1 | 9/2003 | Hall et al. |
| 2003/0208189 A1 | 11/2003 | Payman |
| 2004/0143253 A1 | 7/2004 | Vanney et al. |
| 2004/0153093 A1 | 8/2004 | Donovan |
| 2004/0158261 A1 | 8/2004 | Vu |
| 2004/0176751 A1 | 9/2004 | Weitzner et al. |
| 2004/0186349 A1 | 9/2004 | Ewers et al. |
| 2004/0193146 A1 | 9/2004 | Lee et al. |
| 2004/0210116 A1 | 10/2004 | Nakao |
| 2004/0253079 A1 | 12/2004 | Sanchez |
| 2005/0033270 A1 | 2/2005 | Ramans et al. |
| 2005/0054900 A1 | 3/2005 | Mawn et al. |
| 2005/0159645 A1 | 7/2005 | Bertolero et al. |
| 2005/0177143 A1 | 8/2005 | Bullington et al. |
| 2005/0240178 A1 | 10/2005 | Morley et al. |
| 2005/0261705 A1 | 11/2005 | Gist |
| 2006/0015133 A1 | 1/2006 | Grayzel et al. |
| 2006/0058617 A1 | 3/2006 | Sano et al. |
| 2006/0058813 A1 | 3/2006 | Teague et al. |
| 2006/0116693 A1 | 6/2006 | Weisenburgh |
| 2006/0135963 A1 | 6/2006 | Kick et al. |
| 2006/0156875 A1 | 7/2006 | McRury et al. |
| 2006/0161137 A1 | 7/2006 | Orban et al. |
| 2006/0178556 A1 | 8/2006 | Nasser et al. |
| 2006/0189891 A1 | 8/2006 | Waxman et al. |
| 2007/0016164 A1 | 1/2007 | Dudney et al. |
| 2007/0027443 A1 | 2/2007 | Rose et al. |
| 2007/0027534 A1 | 2/2007 | Bergheim et al. |
| 2007/0032906 A1 | 2/2007 | Sutherland et al. |
| 2007/0083098 A1 | 4/2007 | Stern et al. |
| 2007/0106304 A1 | 5/2007 | Hammack et al. |
| 2007/0123855 A1 | 5/2007 | Morley et al. |
| 2007/0135803 A1 | 6/2007 | Belson |
| 2007/0208375 A1 | 9/2007 | Nishizawa et al. |
| 2007/0213668 A1 | 9/2007 | Spitz |
| 2007/0239178 A1 | 10/2007 | Weitzner et al. |
| 2007/0250111 A1 | 10/2007 | Lu et al. |
| 2007/0276539 A1 | 11/2007 | Habibi et al. |
| 2007/0299427 A1 | 12/2007 | Yeung et al. |
| 2008/0015566 A1 | 1/2008 | Livneh |
| 2008/0021440 A1 | 1/2008 | Solomon |
| 2008/0033467 A1 | 2/2008 | Miyamoto et al. |
| 2008/0045981 A1 | 2/2008 | Margolin et al. |
| 2008/0046122 A1 | 2/2008 | Manzo et al. |
| 2008/0065111 A1 | 3/2008 | Blumenkranz et al. |
| 2008/0065112 A1 | 3/2008 | Tovey et al. |
| 2008/0125698 A1 | 5/2008 | Gerg et al. |
| 2008/0147089 A1 | 6/2008 | Loh |
| 2008/0187101 A1 | 8/2008 | Gertner |
| 2008/0196533 A1 | 8/2008 | Bergamasco et al. |
| 2008/0228104 A1 | 9/2008 | Uber et al. |
| 2009/0005768 A1 | 1/2009 | Sharareh et al. |
| 2009/0012507 A1 | 1/2009 | Culbertson et al. |
| 2009/0030446 A1 | 1/2009 | Measamer |
| 2009/0036900 A1 | 2/2009 | Moll |
| 2009/0043305 A1 | 2/2009 | Brodbeck et al. |
| 2009/0048611 A1 | 2/2009 | Funda et al. |
| 2009/0082634 A1 | 3/2009 | Kathrani et al. |
| 2009/0088774 A1 | 4/2009 | Swarup et al. |

(56) References Cited

U.S. PATENT DOCUMENTS

| | | |
|---|---|---|
| 2009/0105723 A1 | 4/2009 | Dillinger |
| 2009/0131885 A1 | 5/2009 | Akahoshi |
| 2009/0161827 A1 | 6/2009 | Gertner et al. |
| 2009/0192524 A1 | 7/2009 | Itkowitz et al. |
| 2009/0227998 A1 | 9/2009 | Aljuri et al. |
| 2009/0248041 A1 | 10/2009 | Williams et al. |
| 2009/0248043 A1 | 10/2009 | Tierney et al. |
| 2009/0264878 A1 | 10/2009 | Carmel et al. |
| 2009/0270760 A1 | 10/2009 | Leimbach et al. |
| 2009/0287188 A1 | 11/2009 | Golden et al. |
| 2009/0299352 A1 | 12/2009 | Zerfas et al. |
| 2009/0312773 A1 | 12/2009 | Cabrera et al. |
| 2009/0326318 A1 | 12/2009 | Tognaccini et al. |
| 2010/0004642 A1 | 1/2010 | Lumpkin |
| 2010/0010504 A1 | 1/2010 | Simaan et al. |
| 2010/0011900 A1 | 1/2010 | Burbank |
| 2010/0011901 A1 | 1/2010 | Burbank |
| 2010/0016852 A1 | 1/2010 | Manzo et al. |
| 2010/0016853 A1 | 1/2010 | Burbank |
| 2010/0081965 A1 | 4/2010 | Mugan et al. |
| 2010/0082017 A1 | 4/2010 | Zickler et al. |
| 2010/0100045 A1 | 4/2010 | Pravongviengkham et al. |
| 2010/0179632 A1 | 7/2010 | Bruszewski et al. |
| 2010/0204605 A1 | 8/2010 | Blakley et al. |
| 2010/0204646 A1 | 8/2010 | Plicchi et al. |
| 2010/0217235 A1 | 8/2010 | Thorstenson et al. |
| 2010/0225209 A1 | 9/2010 | Goldberg et al. |
| 2010/0228249 A1 | 9/2010 | Mohr et al. |
| 2010/0234857 A1 | 9/2010 | Itkowitz et al. |
| 2010/0268211 A1 | 10/2010 | Manwaring et al. |
| 2010/0286712 A1 | 11/2010 | Won et al. |
| 2010/0312141 A1 | 12/2010 | Keast et al. |
| 2010/0331858 A1 | 12/2010 | Simaan et al. |
| 2011/0015483 A1 | 1/2011 | Barbagli et al. |
| 2011/0028790 A1 | 2/2011 | Farr et al. |
| 2011/0071541 A1 | 3/2011 | Prisco et al. |
| 2011/0071543 A1 | 3/2011 | Prisco et al. |
| 2011/0106146 A1 | 5/2011 | Jeong |
| 2011/0125165 A1 | 5/2011 | Simaan et al. |
| 2011/0152880 A1 | 6/2011 | Alvarez et al. |
| 2011/0160713 A1 | 6/2011 | Neuberger |
| 2011/0160745 A1 | 6/2011 | Fielding et al. |
| 2011/0167611 A1 | 7/2011 | Williams |
| 2011/0184558 A1 | 7/2011 | Jacob et al. |
| 2011/0208211 A1 | 8/2011 | Whitfield et al. |
| 2011/0213362 A1 | 9/2011 | Cunningham et al. |
| 2011/0224660 A1 | 9/2011 | Neuberger et al. |
| 2011/0238064 A1 | 9/2011 | Williams |
| 2011/0257641 A1 | 10/2011 | Hastings et al. |
| 2011/0264112 A1 | 10/2011 | Nowlin et al. |
| 2011/0276085 A1 | 11/2011 | Krzyzanowski |
| 2011/0277775 A1 | 11/2011 | Holop et al. |
| 2011/0313343 A1 | 12/2011 | Milutinovic et al. |
| 2012/0048759 A1 | 3/2012 | Disch et al. |
| 2012/0069167 A1 | 3/2012 | Liu |
| 2012/0138586 A1 | 6/2012 | Webster et al. |
| 2012/0138660 A1 | 6/2012 | Shelton, IV et al. |
| 2012/0209069 A1 | 8/2012 | Popovic |
| 2012/0209315 A1 | 8/2012 | Amat Girbau |
| 2012/0232342 A1 | 9/2012 | Reydel |
| 2012/0253277 A1 | 10/2012 | Tah |
| 2012/0253332 A1 | 10/2012 | Moll |
| 2012/0259320 A1 | 10/2012 | Loesel et al. |
| 2012/0283747 A1 | 11/2012 | Popovic |
| 2012/0296318 A1 | 11/2012 | Wellhöfer et al. |
| 2012/0302869 A1 | 11/2012 | Koyrakh et al. |
| 2013/0006144 A1 | 1/2013 | Clancy et al. |
| 2013/0035537 A1 | 2/2013 | Wallace et al. |
| 2013/0053877 A1 | 2/2013 | BenMaamer et al. |
| 2013/0066136 A1 | 3/2013 | Palese et al. |
| 2013/0085442 A1 | 4/2013 | Shtul et al. |
| 2013/0085486 A1 | 4/2013 | Boutoussov et al. |
| 2013/0096422 A1 | 4/2013 | Boctor et al. |
| 2013/0096574 A1 | 4/2013 | Kang et al. |
| 2013/0110042 A1 | 5/2013 | Humphreys |
| 2013/0110107 A1 | 5/2013 | Smith et al. |
| 2013/0116716 A1 | 5/2013 | Bahls et al. |
| 2013/0144274 A1 | 6/2013 | Stefanchik et al. |
| 2013/0144395 A1 | 6/2013 | Stefanchik et al. |
| 2013/0190796 A1 | 7/2013 | Tilson et al. |
| 2013/0225997 A1 | 8/2013 | Dillard et al. |
| 2013/0226161 A1 | 8/2013 | Hickenbotham |
| 2013/0233908 A1 | 9/2013 | Knodel et al. |
| 2013/0253267 A1 | 9/2013 | Collins |
| 2013/0303876 A1 | 11/2013 | Gelfand et al. |
| 2013/0310819 A1 | 11/2013 | Neuberger et al. |
| 2013/0317519 A1 | 11/2013 | Romo et al. |
| 2013/0325030 A1 | 12/2013 | Hourtash |
| 2013/0334281 A1 | 12/2013 | Williams |
| 2013/0345686 A1 | 12/2013 | Brown |
| 2014/0005681 A1 | 1/2014 | Gee et al. |
| 2014/0022353 A1* | 1/2014 | Hamersma ......... G05B 19/4061 348/46 |
| 2014/0039517 A1 | 2/2014 | Bowling et al. |
| 2014/0039681 A1 | 2/2014 | Bowling et al. |
| 2014/0046308 A1 | 2/2014 | Bischoff et al. |
| 2014/0051049 A1 | 2/2014 | Jarc et al. |
| 2014/0051985 A1 | 2/2014 | Fan et al. |
| 2014/0058365 A1 | 2/2014 | Bille et al. |
| 2014/0058404 A1 | 2/2014 | Hammack et al. |
| 2014/0058428 A1 | 2/2014 | Christopher et al. |
| 2014/0100445 A1 | 4/2014 | Stenzel et al. |
| 2014/0142591 A1 | 5/2014 | Alvarez et al. |
| 2014/0163318 A1 | 6/2014 | Swanstrom |
| 2014/0163736 A1 | 6/2014 | Azizian et al. |
| 2014/0194859 A1 | 7/2014 | Ianchulev |
| 2014/0194905 A1 | 7/2014 | Kappel et al. |
| 2014/0222207 A1 | 8/2014 | Bowling et al. |
| 2014/0243801 A1 | 8/2014 | Fanelli et al. |
| 2014/0243849 A1 | 8/2014 | Saglam et al. |
| 2014/0246473 A1 | 9/2014 | Auld |
| 2014/0257333 A1 | 9/2014 | Blumenkranz |
| 2014/0275956 A1 | 9/2014 | Fan |
| 2014/0276723 A1 | 9/2014 | Parihar et al. |
| 2014/0276956 A1 | 9/2014 | Crainich et al. |
| 2014/0309655 A1 | 10/2014 | Gal et al. |
| 2014/0316203 A1 | 10/2014 | Carroux et al. |
| 2014/0357984 A1 | 12/2014 | Wallace et al. |
| 2015/0025549 A1 | 1/2015 | Kilroy et al. |
| 2015/0045675 A1 | 2/2015 | Chernomorsky |
| 2015/0073439 A1 | 3/2015 | Dannaher |
| 2015/0080879 A1 | 3/2015 | Trees et al. |
| 2015/0088161 A1 | 3/2015 | Hata et al. |
| 2015/0127045 A1 | 5/2015 | Prestel |
| 2015/0133960 A1 | 5/2015 | Lohmeier et al. |
| 2015/0150635 A1 | 6/2015 | Kilroy et al. |
| 2015/0164522 A1 | 6/2015 | Budiman et al. |
| 2015/0190204 A1 | 7/2015 | Popovi |
| 2015/0201917 A1 | 7/2015 | Snow |
| 2015/0202085 A1 | 7/2015 | Lemonis et al. |
| 2015/0223832 A1 | 8/2015 | Swaney et al. |
| 2015/0297299 A1 | 10/2015 | Yeung et al. |
| 2015/0305650 A1 | 10/2015 | Hunter et al. |
| 2015/0314110 A1 | 11/2015 | Park |
| 2015/0366629 A1 | 12/2015 | Bowling et al. |
| 2015/0374446 A1 | 12/2015 | Malackowski et al. |
| 2016/0022289 A1 | 1/2016 | Wan |
| 2016/0022466 A1 | 1/2016 | Pedtke et al. |
| 2016/0030073 A1 | 2/2016 | Isakov et al. |
| 2016/0045208 A1 | 2/2016 | Ciulla |
| 2016/0051318 A1 | 2/2016 | Manzo et al. |
| 2016/0066935 A1 | 3/2016 | Nguyen et al. |
| 2016/0158490 A1 | 6/2016 | Leeflang et al. |
| 2016/0183841 A1 | 6/2016 | Duindam et al. |
| 2016/0199984 A1 | 7/2016 | Lohmeier et al. |
| 2016/0235495 A1 | 8/2016 | Wallace et al. |
| 2016/0242858 A1 | 8/2016 | Moctezuma De La Barrera et al. |
| 2016/0249932 A1 | 9/2016 | Rogers et al. |
| 2016/0270865 A1 | 9/2016 | Landey et al. |
| 2016/0287279 A1 | 10/2016 | Bovay et al. |
| 2016/0302871 A1 | 10/2016 | Gregerson et al. |
| 2016/0303743 A1 | 10/2016 | Rockrohr |
| 2016/0310146 A1 | 10/2016 | Levy et al. |
| 2016/0314710 A1 | 10/2016 | Jarc |

(56) References Cited

U.S. PATENT DOCUMENTS

| | | |
|---|---|---|
| 2016/0331358 A1 | 11/2016 | Gordon |
| 2016/0367324 A1 | 12/2016 | Sato et al. |
| 2017/0000577 A1 | 1/2017 | Bowling et al. |
| 2017/0007337 A1 | 1/2017 | Dan |
| 2017/0010620 A1* | 1/2017 | Watabe .............. G05D 1/0248 |
| 2017/0020615 A1 | 1/2017 | Koenig et al. |
| 2017/0049471 A1 | 2/2017 | Gaffney et al. |
| 2017/0055995 A1 | 3/2017 | Weir et al. |
| 2017/0056117 A1 | 3/2017 | Hourtash et al. |
| 2017/0065227 A1 | 3/2017 | Marrs et al. |
| 2017/0071456 A1 | 3/2017 | Ratnakar |
| 2017/0071584 A1 | 3/2017 | Suigetsu et al. |
| 2017/0086934 A1 | 3/2017 | Devengenzo et al. |
| 2017/0095234 A1 | 4/2017 | Prisco et al. |
| 2017/0095295 A1 | 4/2017 | Overmyer |
| 2017/0095299 A1 | 4/2017 | Hendrick et al. |
| 2017/0135706 A1 | 5/2017 | Frey et al. |
| 2017/0135710 A1 | 5/2017 | Hasegawa et al. |
| 2017/0135833 A1 | 5/2017 | Syed |
| 2017/0143442 A1 | 5/2017 | Tesar et al. |
| 2017/0151416 A1 | 6/2017 | Kutikov et al. |
| 2017/0165009 A1 | 6/2017 | Chaplin et al. |
| 2017/0172553 A1 | 6/2017 | Chaplin et al. |
| 2017/0172680 A1 | 6/2017 | Bowling et al. |
| 2017/0189118 A1 | 7/2017 | Chopra et al. |
| 2017/0189131 A1 | 7/2017 | Weir |
| 2017/0202627 A1 | 7/2017 | Sramek et al. |
| 2017/0209073 A1 | 7/2017 | Sramek et al. |
| 2017/0252096 A1 | 9/2017 | Felder et al. |
| 2017/0258534 A1 | 9/2017 | Hourtash et al. |
| 2017/0265923 A1 | 9/2017 | Privitera et al. |
| 2017/0265954 A1 | 9/2017 | Burbank et al. |
| 2017/0281145 A1* | 10/2017 | Crawford .......... A61B 17/1703 |
| 2017/0290631 A1 | 10/2017 | Lee et al. |
| 2017/0296277 A1 | 10/2017 | Hourtash |
| 2017/0319289 A1 | 11/2017 | Neff et al. |
| 2017/0333145 A1 | 11/2017 | Griffiths et al. |
| 2017/0333147 A1 | 11/2017 | Bernstein |
| 2018/0000563 A1 | 1/2018 | Shanjani et al. |
| 2018/0025666 A1 | 1/2018 | Ho et al. |
| 2018/0036884 A1* | 2/2018 | Chen .................. A61B 34/30 |
| 2018/0049824 A1 | 2/2018 | Harris et al. |
| 2018/0078439 A1* | 3/2018 | Cagle ................. A61B 34/30 |
| 2018/0079090 A1 | 3/2018 | Koenig et al. |
| 2018/0080841 A1 | 3/2018 | Cordoba et al. |
| 2018/0098817 A1 | 4/2018 | Nichogi |
| 2018/0140371 A1 | 5/2018 | Hares et al. |
| 2018/0193049 A1 | 7/2018 | Heck et al. |
| 2018/0206931 A1 | 7/2018 | Scheib |
| 2018/0221038 A1 | 8/2018 | Noonan et al. |
| 2018/0221039 A1 | 8/2018 | Shah |
| 2018/0250085 A1 | 9/2018 | Simi et al. |
| 2018/0263714 A1* | 9/2018 | Kostrzewski .......... A61B 34/76 |
| 2018/0279852 A1 | 10/2018 | Rafii-Tari et al. |
| 2018/0289431 A1 | 10/2018 | Draper et al. |
| 2018/0296285 A1 | 10/2018 | Simi et al. |
| 2018/0325499 A1 | 11/2018 | Landey et al. |
| 2018/0338799 A1 | 11/2018 | Hladio et al. |
| 2018/0360435 A1 | 12/2018 | Romo |
| 2018/0368920 A1 | 12/2018 | Ummalaneni |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0015166 A1 | 1/2019 | Mahoney et al. |
| 2019/0047154 A1 | 2/2019 | Itkowitz et al. |
| 2019/0054620 A1 | 2/2019 | Griffiths et al. |
| 2019/0069962 A1 | 3/2019 | Tabandeh et al. |
| 2019/0099231 A1 | 4/2019 | Bruehwiler et al. |
| 2019/0099232 A1 | 4/2019 | Soto et al. |
| 2019/0107454 A1 | 4/2019 | Lin |
| 2019/0110839 A1 | 4/2019 | Rafii-Tari et al. |
| 2019/0117320 A1 | 4/2019 | Shoham et al. |
| 2019/0117324 A1 | 4/2019 | Hibner et al. |
| 2019/0133689 A1* | 5/2019 | Johnson .............. G06F 3/011 |
| 2019/0151148 A1 | 5/2019 | Alvarez et al. |
| 2019/0159848 A1 | 5/2019 | Quaid et al. |
| 2019/0167366 A1 | 6/2019 | Ummalaneni et al. |
| 2019/0175009 A1 | 6/2019 | Mintz et al. |
| 2019/0183585 A1 | 6/2019 | Rafii-Tari et al. |
| 2019/0183587 A1 | 6/2019 | Rafii-Tari et al. |
| 2019/0192249 A1 | 6/2019 | Bowling et al. |
| 2019/0216548 A1 | 7/2019 | Ummalaneni |
| 2019/0216550 A1 | 7/2019 | Eyre et al. |
| 2019/0216576 A1 | 7/2019 | Eyre et al. |
| 2019/0223974 A1 | 7/2019 | Romo et al. |
| 2019/0231460 A1 | 8/2019 | DiMaio et al. |
| 2019/0239890 A1 | 8/2019 | Stokes et al. |
| 2019/0262084 A1* | 8/2019 | Roh .................. G16H 20/40 |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298460 A1 | 10/2019 | Al-Jadda et al. |
| 2019/0298464 A1 | 10/2019 | Abbott |
| 2019/0298465 A1 | 10/2019 | Chin et al. |
| 2019/0298469 A1 | 10/2019 | Ramstad et al. |
| 2019/0314616 A1 | 10/2019 | Moll et al. |
| 2019/0336238 A1 | 11/2019 | Yu et al. |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0375383 A1 | 12/2019 | Alvarez |
| 2019/0380787 A1 | 12/2019 | Ye et al. |
| 2019/0380797 A1 | 12/2019 | Yu et al. |
| 2020/0000533 A1 | 1/2020 | Schuh et al. |
| 2020/0030046 A1 | 1/2020 | Bowling et al. |
| 2020/0038123 A1 | 2/2020 | Graetzel et al. |
| 2020/0039086 A1 | 2/2020 | Meyer et al. |
| 2020/0046434 A1 | 2/2020 | Graetzel et al. |
| 2020/0060516 A1 | 2/2020 | Baez, Jr. |
| 2020/0085516 A1 | 3/2020 | DeFonzo et al. |
| 2020/0093549 A1 | 3/2020 | Chin et al. |
| 2020/0093554 A1 | 3/2020 | Schuh et al. |
| 2020/0100855 A1 | 4/2020 | Leparmentier et al. |
| 2020/0107894 A1 | 4/2020 | Wallace et al. |
| 2020/0121502 A1 | 4/2020 | Kintz |
| 2020/0138531 A1 | 5/2020 | Chaplin |
| 2020/0146769 A1 | 5/2020 | Eyre et al. |
| 2020/0163726 A1 | 5/2020 | Tanner et al. |
| 2020/0170720 A1 | 6/2020 | Ummalaneni |
| 2020/0171660 A1 | 6/2020 | Ho et al. |
| 2020/0188043 A1 | 6/2020 | Yu et al. |
| 2020/0197109 A1 | 6/2020 | Chaplin |
| 2020/0197112 A1 | 6/2020 | Chin et al. |
| 2020/0206472 A1 | 7/2020 | Ma et al. |
| 2020/0217733 A1 | 7/2020 | Lin et al. |
| 2020/0222134 A1 | 7/2020 | Schuh et al. |
| 2020/0237458 A1 | 7/2020 | DeFonzo et al. |
| 2020/0261172 A1 | 8/2020 | Romo et al. |
| 2020/0268459 A1 | 8/2020 | Noonan et al. |
| 2020/0268460 A1 | 8/2020 | Tse et al. |
| 2020/0281787 A1 | 9/2020 | Ruiz |
| 2020/0297437 A1 | 9/2020 | Schuh et al. |
| 2020/0297444 A1 | 9/2020 | Camarillo et al. |
| 2020/0305983 A1 | 10/2020 | Yampolsky et al. |
| 2020/0305989 A1 | 10/2020 | Schuh et al. |
| 2020/0305992 A1 | 10/2020 | Schuh et al. |
| 2020/0315717 A1 | 10/2020 | Bovay et al. |
| 2020/0315723 A1 | 10/2020 | Hassan et al. |
| 2020/0323596 A1 | 10/2020 | Moll et al. |
| 2020/0330167 A1 | 10/2020 | Romo et al. |
| 2020/0335207 A1* | 10/2020 | Kara .................. G16H 40/67 |
| 2020/0345216 A1 | 11/2020 | Jenkins |
| 2020/0352420 A1 | 11/2020 | Graetzel et al. |
| 2020/0360183 A1 | 11/2020 | Alvarez et al. |
| 2020/0367726 A1 | 11/2020 | Landey et al. |
| 2020/0367981 A1 | 11/2020 | Ho et al. |
| 2020/0375678 A1 | 12/2020 | Wallace et al. |
| 2020/0405375 A1 | 12/2020 | Shelton, IV et al. |
| 2020/0405403 A1 | 12/2020 | Shelton, IV et al. |
| 2020/0405406 A1* | 12/2020 | Harris .................. A61B 46/40 |
| 2020/0405414 A1 | 12/2020 | Shelton, IV et al. |
| 2021/0068908 A1* | 3/2021 | Thienphrapa .......... A61B 34/35 |

(56) References Cited

U.S. PATENT DOCUMENTS

| | | | |
|---|---|---|---|
| 2021/0275275 A1* | 9/2021 | Toporek | A61B 34/30 |
| 2022/0022984 A1 | 1/2022 | Peine et al. | |
| 2023/0285094 A1 | 9/2023 | Huang et al. | |

FOREIGN PATENT DOCUMENTS

| | | |
|---|---|---|
| CN | 103298414 A | 9/2013 |
| CN | 104619281 A | 5/2015 |
| CN | 205729413 U | 11/2016 |
| EP | 0 347 098 | 2/1996 |
| EP | 0347098 B1 | 2/1996 |
| EP | 1321106 A1 | 6/2003 |
| EP | 1849423 A2 | 10/2007 |
| JP | 2005-270464 A | 10/2005 |
| WO | 2006/124390 A2 | 11/2006 |
| WO | WO 06/124390 | 11/2006 |
| WO | 2011/161218 A1 | 12/2011 |
| WO | 2013/107468 A1 | 7/2013 |
| WO | 2015/153174 A1 | 10/2015 |
| WO | 2016/137612 A1 | 9/2016 |
| WO | 2017/048194 A1 | 3/2017 |
| WO | WO 17/048194 | 3/2017 |
| WO | 2017/114855 A1 | 7/2017 |
| WO | 2018/069679 A1 | 4/2018 |
| WO | 2018/189722 A1 | 10/2018 |
| WO | WO 2019/136039 | 7/2019 |

OTHER PUBLICATIONS

Aghakhani et al., May 6, 2013, Task control with remote center of motion constraint for minimally invasive robotic surgery, 2013 IEEE International Conference on Robotics and Automation, pp. 5807-5812.

Darwiche, 2015, Operative technique and early experience for robotic assisted laparoscopic nephroureterectomy (RALNU) using da Vinci XI, SpringerPlus, 4:298.

Sasaki, 2017, Laparoscopic hemicolectomy for a patient with situs inversus totalis: a case report, Int. J. Surg. Case Rep. 41:93-96.

PCT International Search Report and PCT Written Opinion of the International Searching Authority; Application No. PCT/IB2020/058717; Dec. 22, 2020; 20 pages.

Aghakhani, Nastaran, et al. "Task control with remote center of motion constraint for minimally invasive robotic surgery." 2013 *IEEE international conference on robotics and automation*. IEEE, 2013.

Darwiche, Fadi, et al. "Operative technique and early experience for robotic-assisted laparoscopic nephroureterectomy (RALNU) using da Vinci Xi." *Springerplus* 4 (2015): 1-5.

Hernansanz, Albert, Alicia Casals, and Josep Amat. "A multi-robot cooperation strategy for dexterous task oriented teleoperation." *Robotics and Autonomous Systems* 68 (2015): 156-172.

Ramezanifard, R., et al. "A novel modeling approach for collision avoidance in robotic surgery." *American Journal of Applied Sciences* 4 (9) (2007): 693-699.

Sasaki, Kazuhito, et al. "Laparoscopic hemicolectomy for a patient with situs inversus totalis: A case report." *International journal of surgery case reports* 41 (2017): 93-96.

European Examination Report dated Dec. 18, 2024, for Application No. 20786049.5, 9 pages.

International Preliminary Report on Patentability dated Apr. 7, 2022, for International Application No. PCT/IB2020/058715, 14 pages.

U.S. Appl. No. 62/906,612, entitled "Systems and Methods for Collision Detection and Avoidance," filed Sep. 26, 2019.

U.S. Appl. No. 62/906,613, entitled "Systems and Methods for Collision Avoidance Using Object Models," filed Sep. 26, 2019.

* cited by examiner

SYSTEMS AND METHODS FOR COLLISION AVOIDANCE USING OBJECT MODELS

CROSS-REFERENCE TO RELATED APPLICATION(S)

This application claims the benefit of U.S. Provisional Application No. 62/906,613, filed Sep. 26, 2019, which is hereby incorporated by reference in its entirety.

TECHNICAL FIELD

The systems and methods disclosed herein are directed to surgical robotics, and more particularly to avoiding robotic arm collisions.

BACKGROUND

Medical procedures, such as laparoscopy, may involve accessing and visualizing an internal region of a patient. In a laparoscopic procedure, a medical tool can be inserted into the internal region through a laparoscopic cannula.

In certain procedures, a robotically-enabled medical system may be used to control the insertion and/or manipulation of one or more medical tool(s). The robotically-enabled medical system may a plurality of robotic arms which control the medical tool(s). In positioning the medical tool(s), portions of the robotic arms may move towards another robotic arm or other object in the environment, which can result in collisions between robotic arm(s) and/or other object(s).

SUMMARY

The systems, methods and devices of this disclosure each have several innovative aspects, no single one of which is solely responsible for the desirable attributes disclosed herein.

In one aspect, there is provided a robotic medical system, comprising: a platform; one or more robotic arms coupled to the platform; a console configured to receive input commanding motion of the one or more robotic arms; a processor; and at least one computer-readable memory in communication with the processor and having stored thereon a model of the one or more robotic arms and computer-executable instructions to cause the processor to: control movement of the one or more robotic arms in a workspace based on the input received by the console, receive an indication of one or more objects are within reach of the one or more robotic arms, and update the model to include a representation of the one or more objects in the workspace.

In another aspect, there is provided a robotic medical system, comprising: a platform; one or more robotic arms coupled to the platform; a console configured to receive input commanding motion of the one or more robotic arms; a processor; and at least one computer-readable memory in communication with the processor and having stored thereon a model of the one or more robotic arms, a database of pre-modeled objects, and computer-executable instructions to cause the processor to: control movement of one or more robotic arms based on the input received by the console, receive an indication of one or more pre-modeled objects being within reach of the one or more robotic arms, and update the model to include a representation of the one or more pre-modeled objects based on the indication and the database.

In yet another aspect, there is provided a robotic medical system, comprising: a platform; one or more robotic arms coupled to the platform; a console configured to receive user input; a processor; and at least one computer-readable memory in communication with the processor and having stored thereon a model of the one or more robotic arms and the platform and computer-executable instructions to cause the processor to: receive an indication of one or more keep-out zones based on the user input received at the console, update the model to include the one or more keep-out zones, and prevent movement of the one or more robotic arms into the one or more keep-out zones based on the updated model.

In still yet another aspect, there is provided a robotic medical system, comprising: a platform; one or more robotic arms coupled to the platform; one or more sensors positioned on the platform and configured to detect one or more objects in a workspace of the robotic arms; a processor; and at least one computer-readable memory in communication with the processor and having stored thereon a model of the one or more robotic arms and the platform and computer-executable instructions to cause the processor to: receive an indication of the one or more objects from the one or more sensors, and update the model, based on the indication, to include the one or more objects within the workspace.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
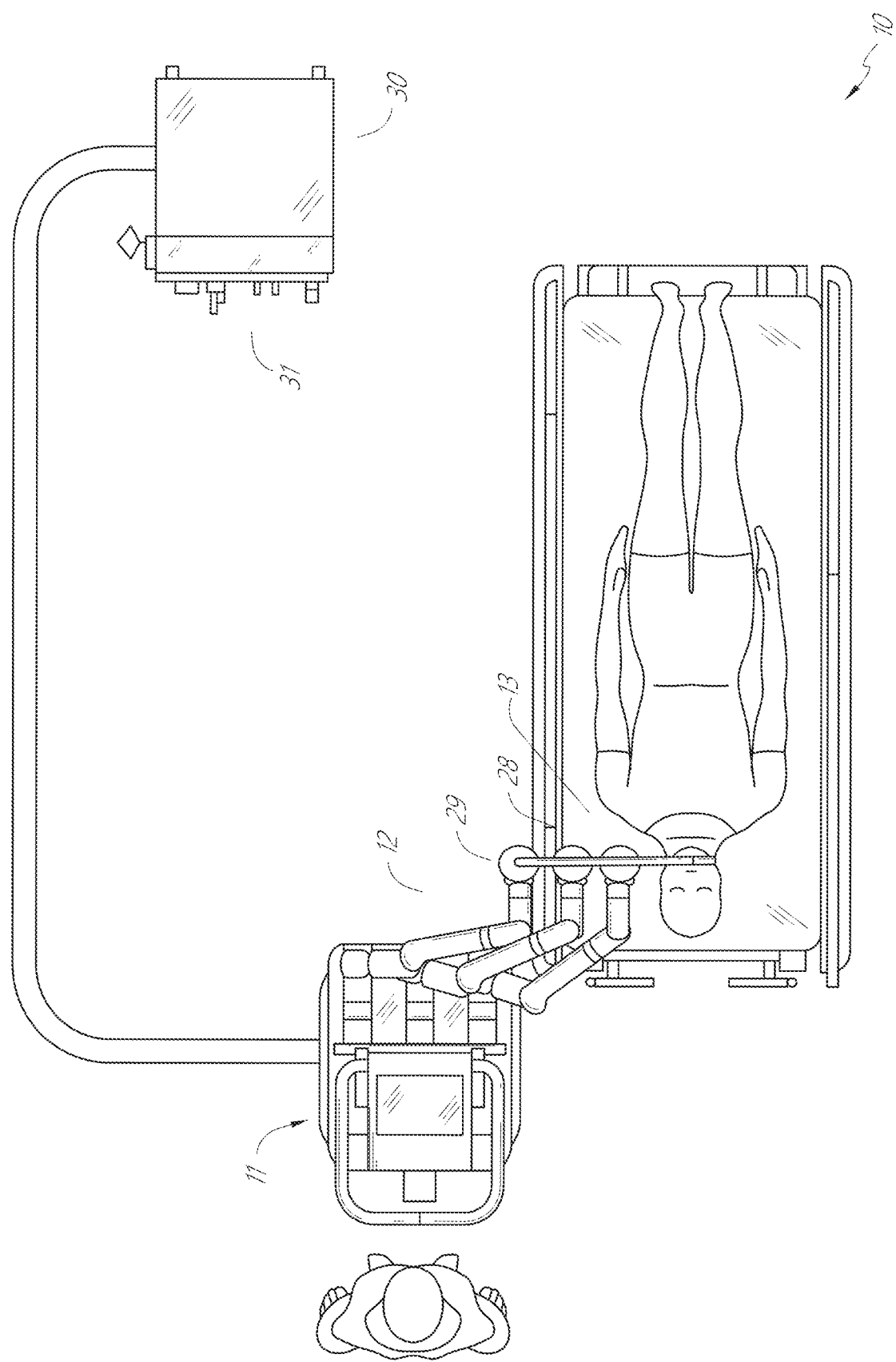
FIG. 1 illustrates an embodiment of a cart-based robotic system arranged for diagnostic and/or therapeutic bronchoscopy.
Figure 2:
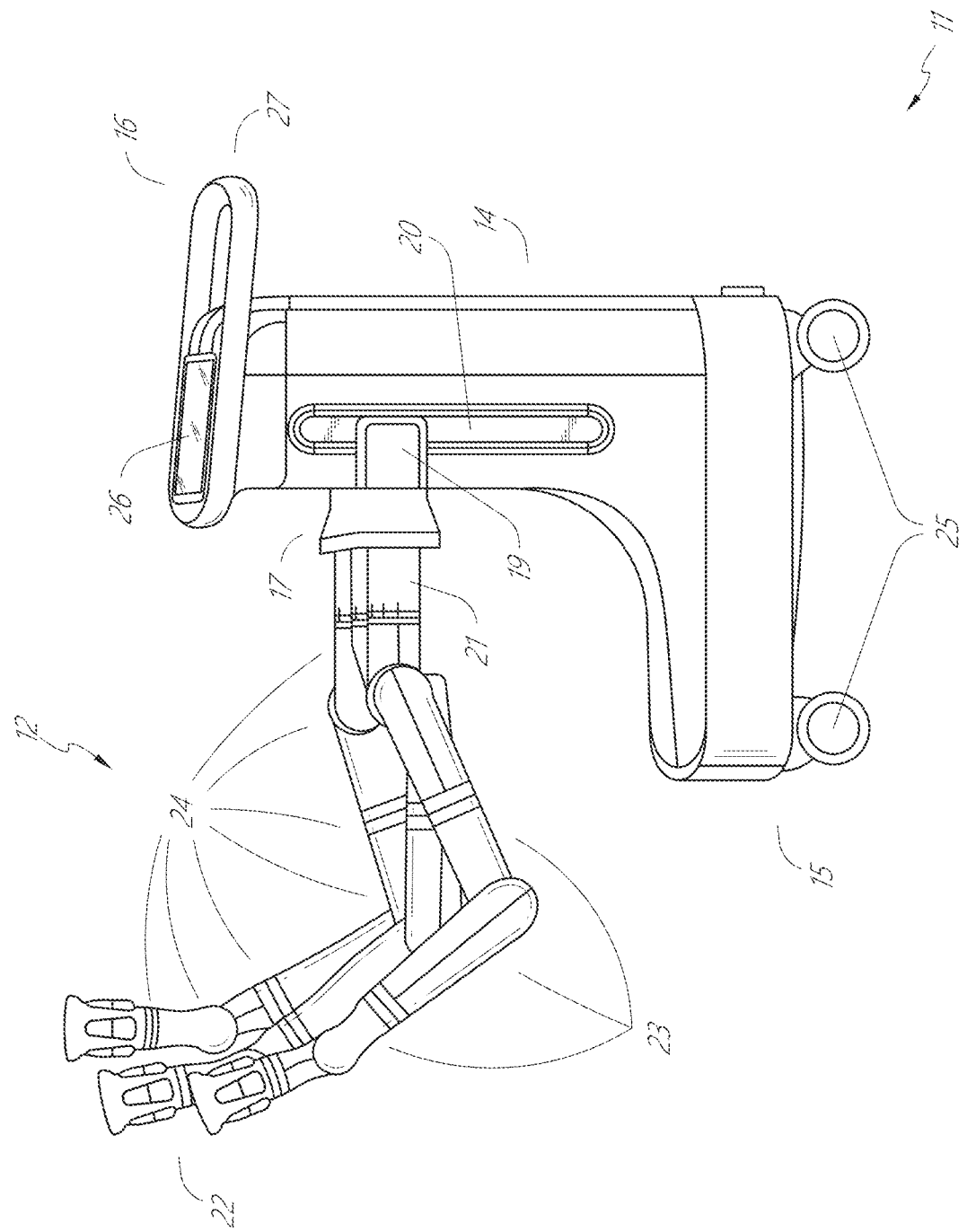
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or repositioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree-of-freedom (DoF) available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
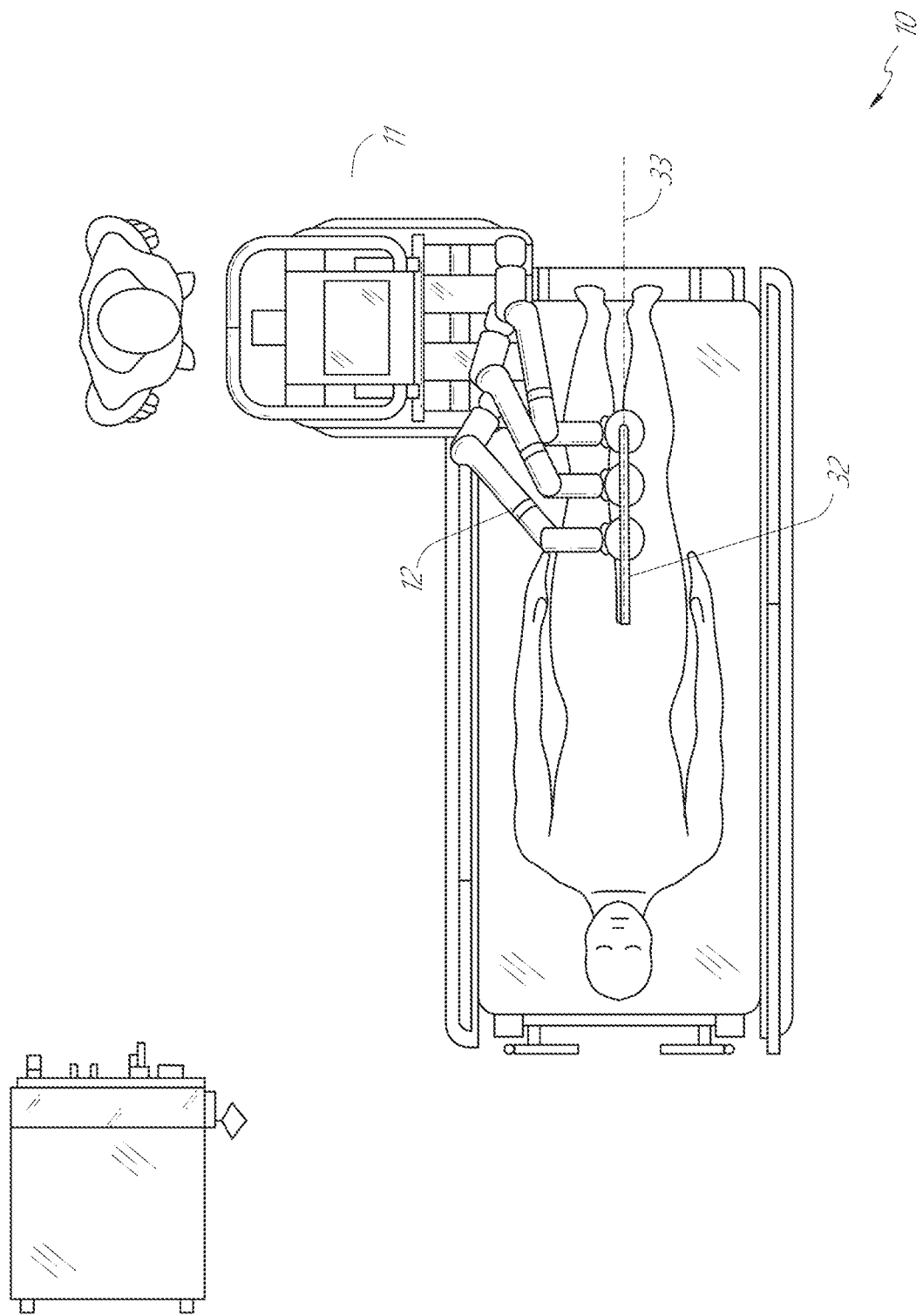
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
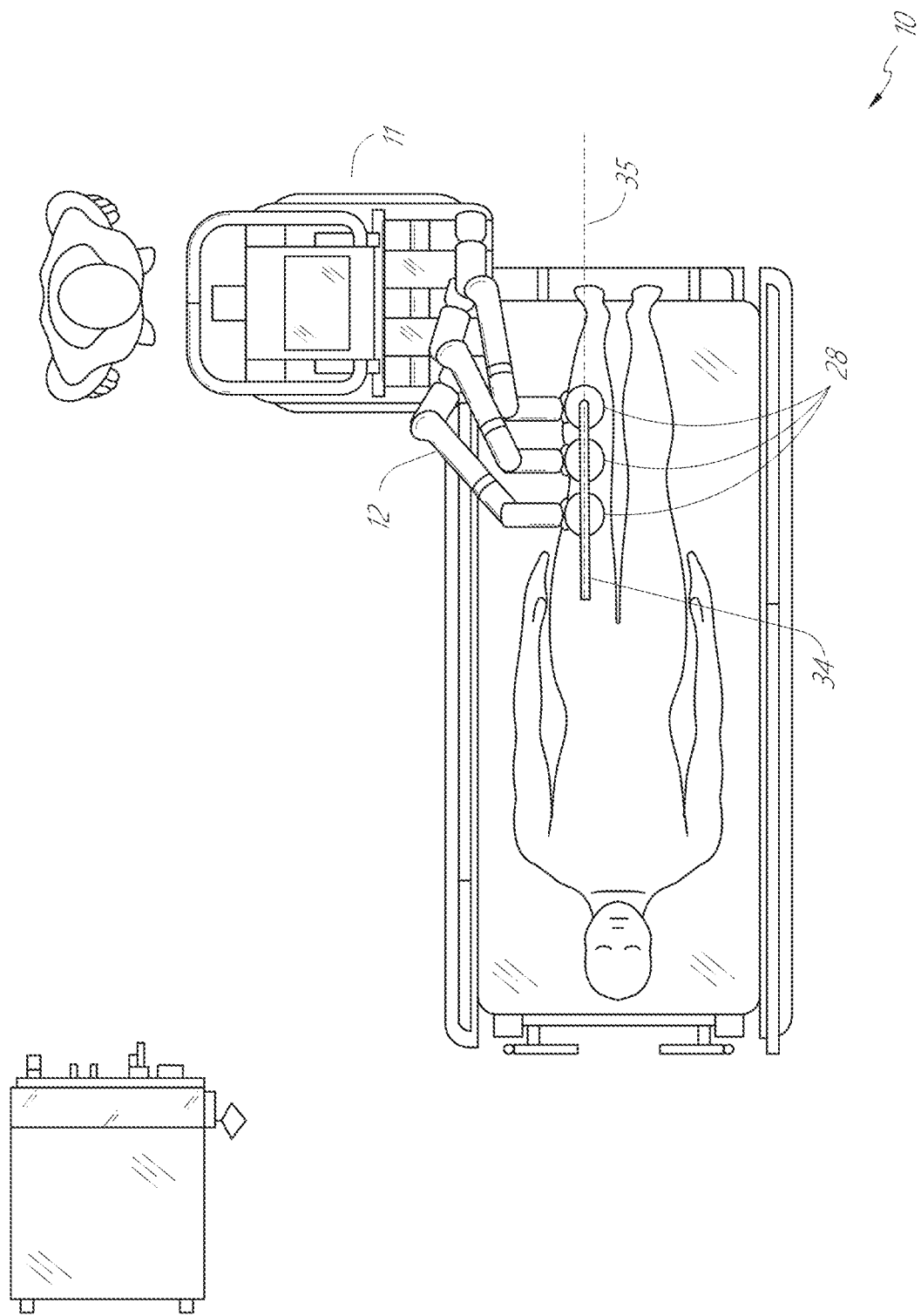
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
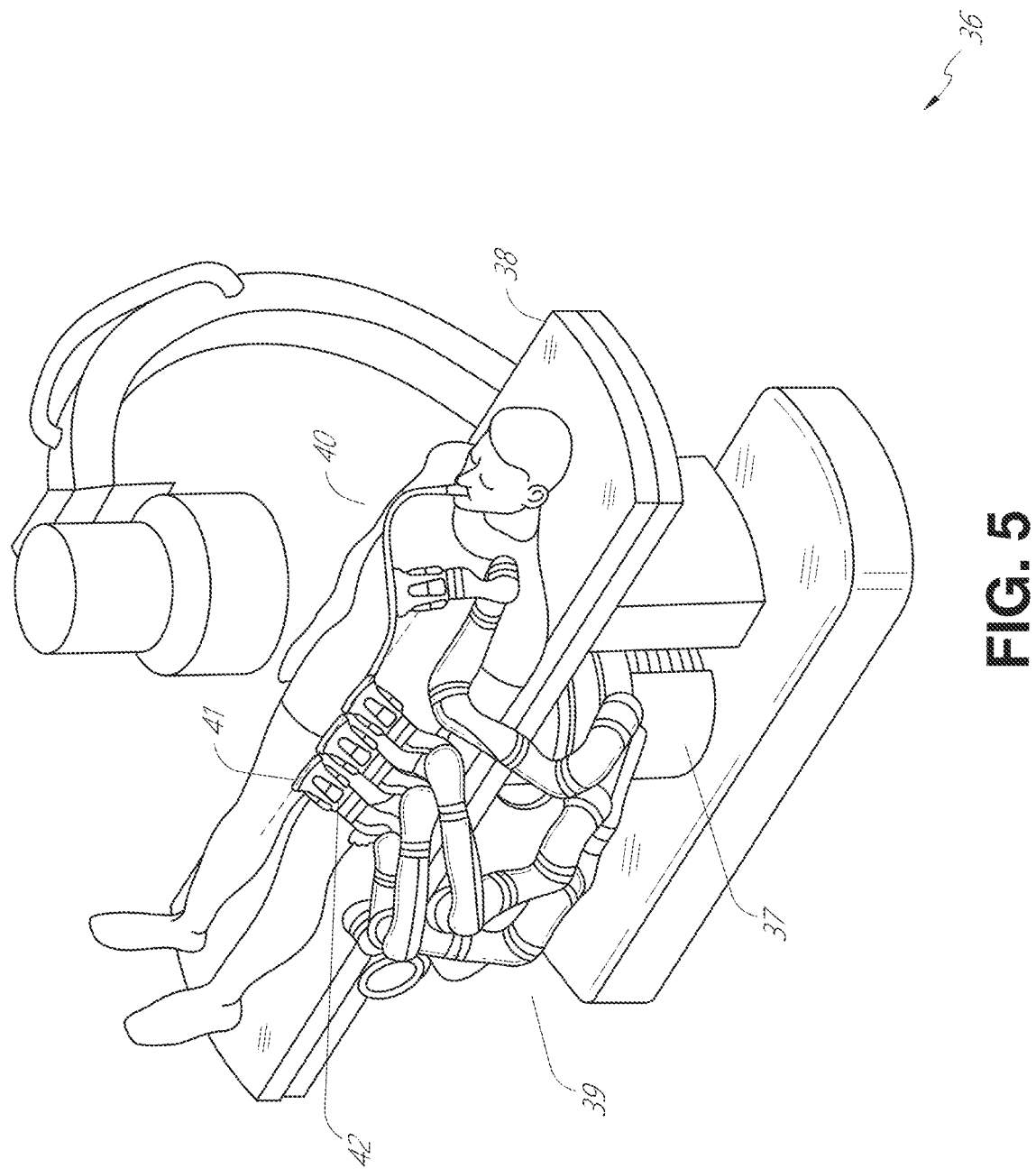
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
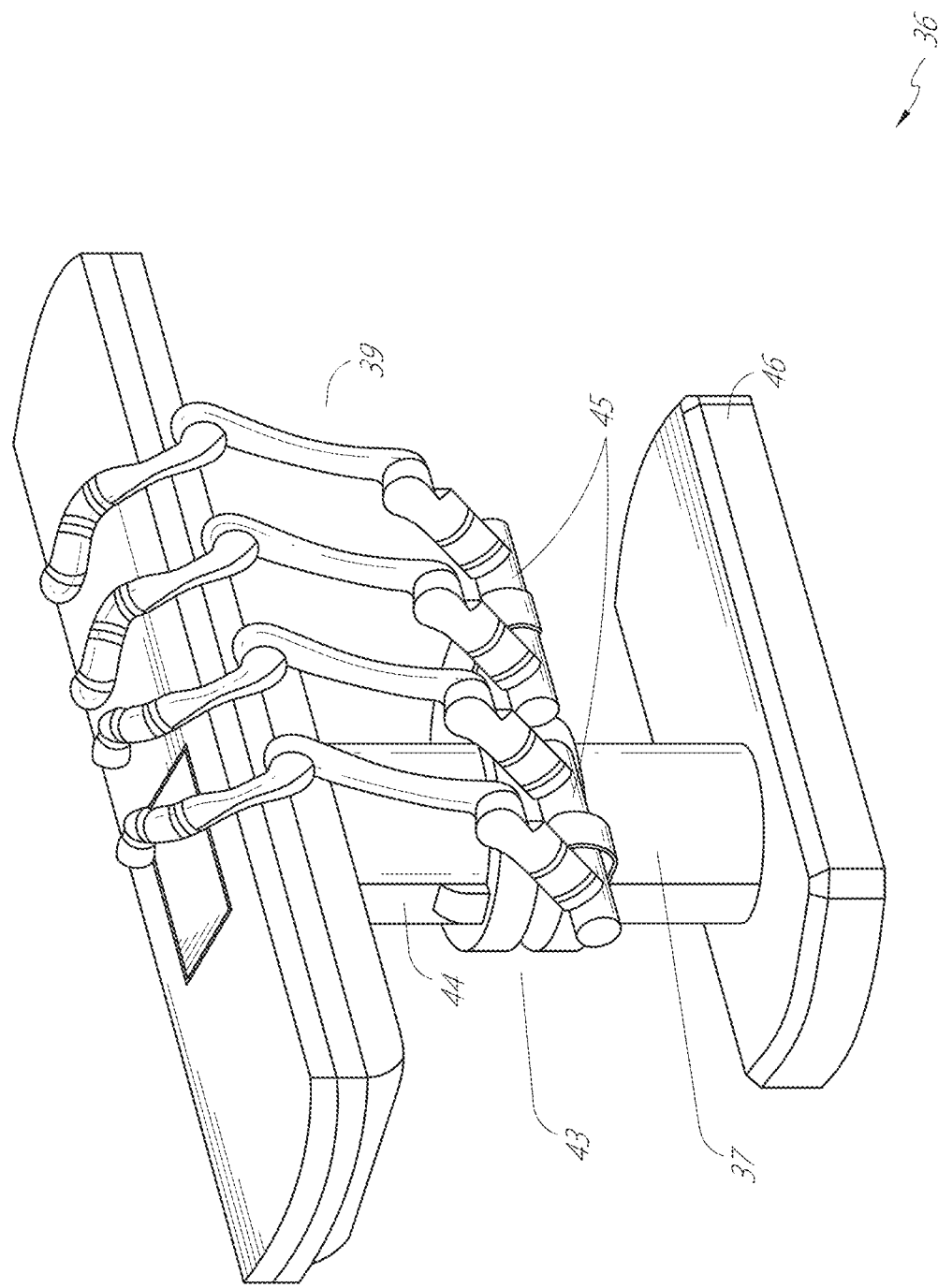
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
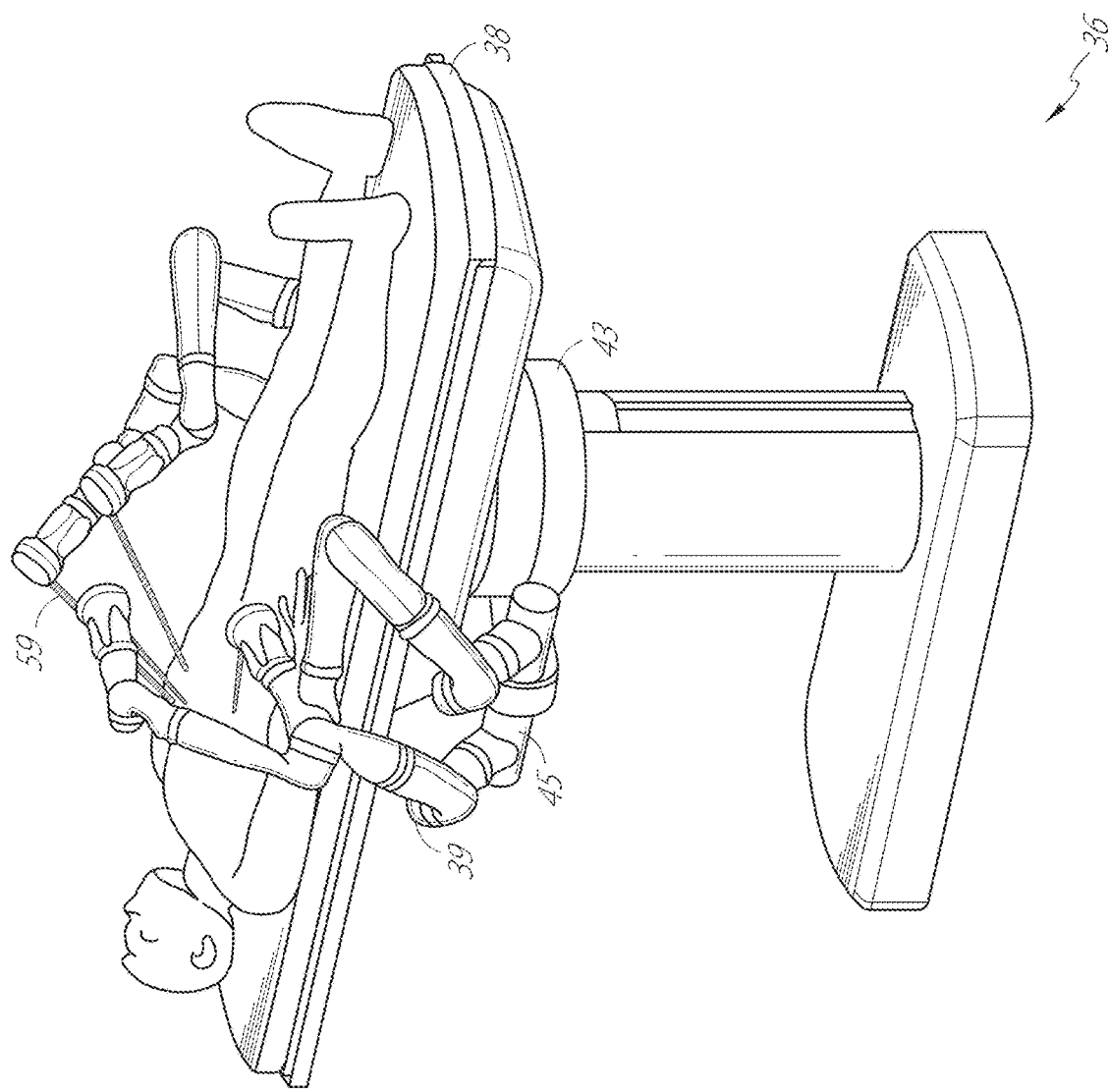
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intra-operative information, such as real-time imaging, navigation, and tracking information. In some embodiments, the tower may also contain holders for gas tanks to be used for insufflation.

Figure 7:
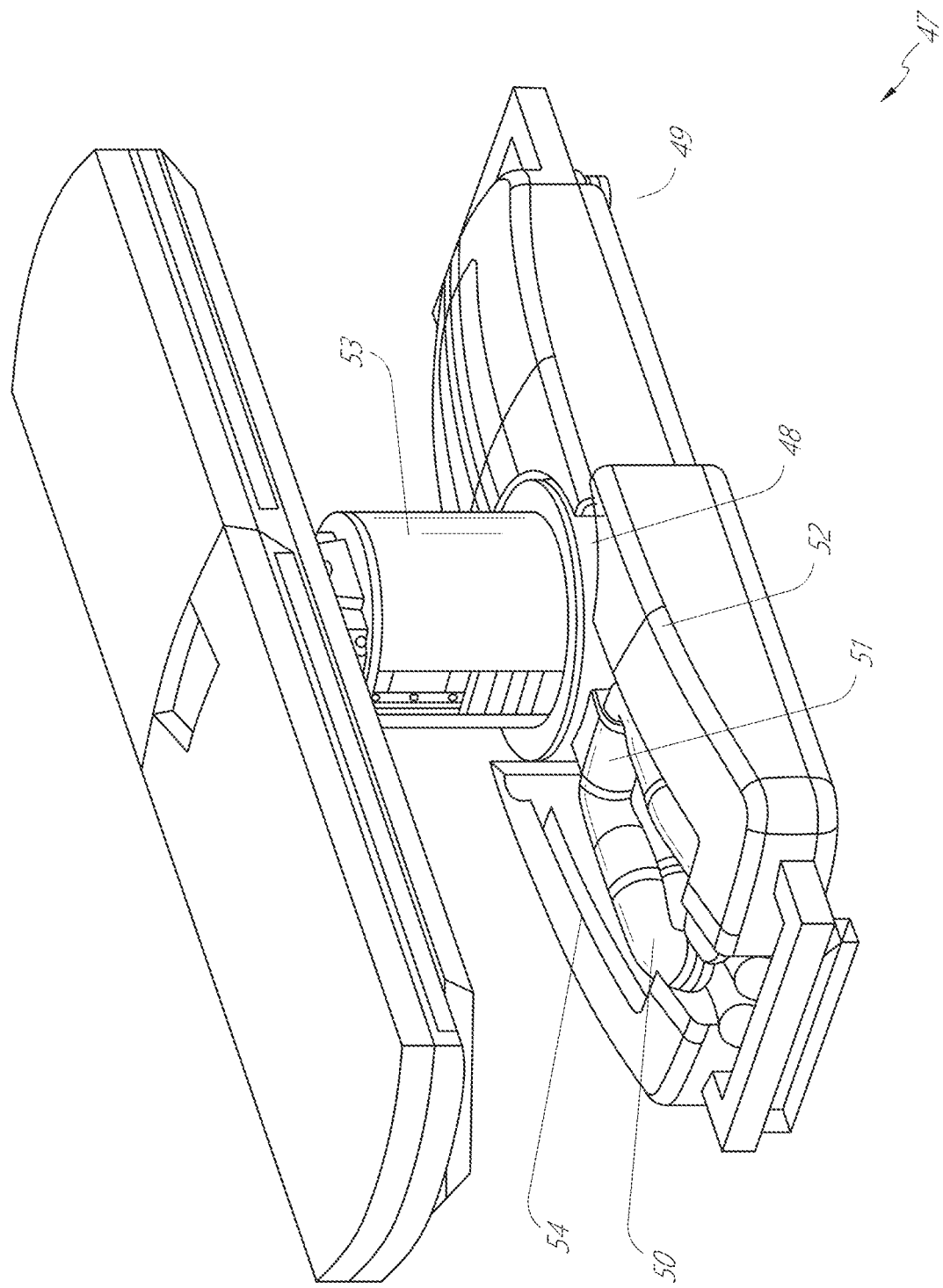
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
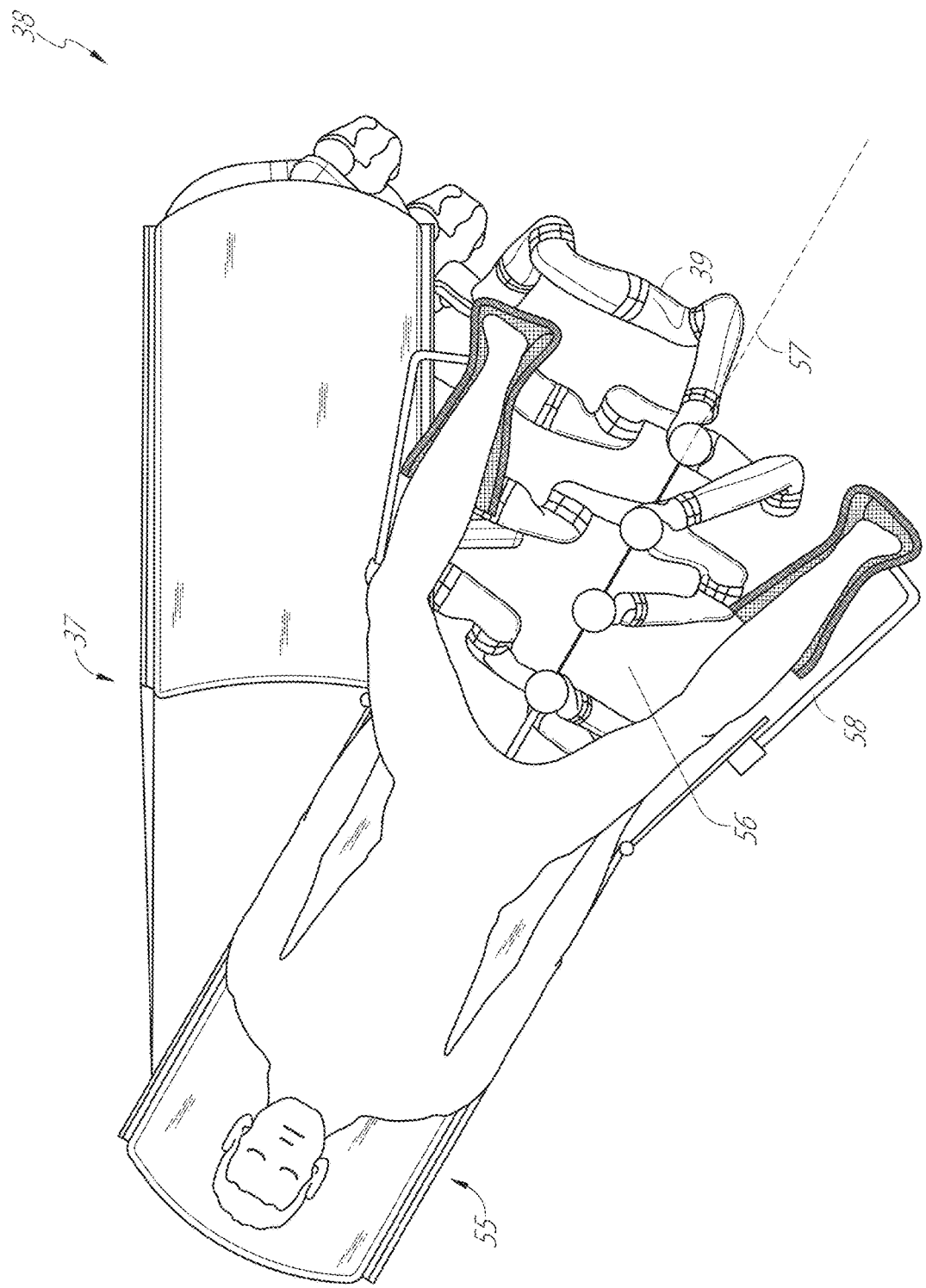
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
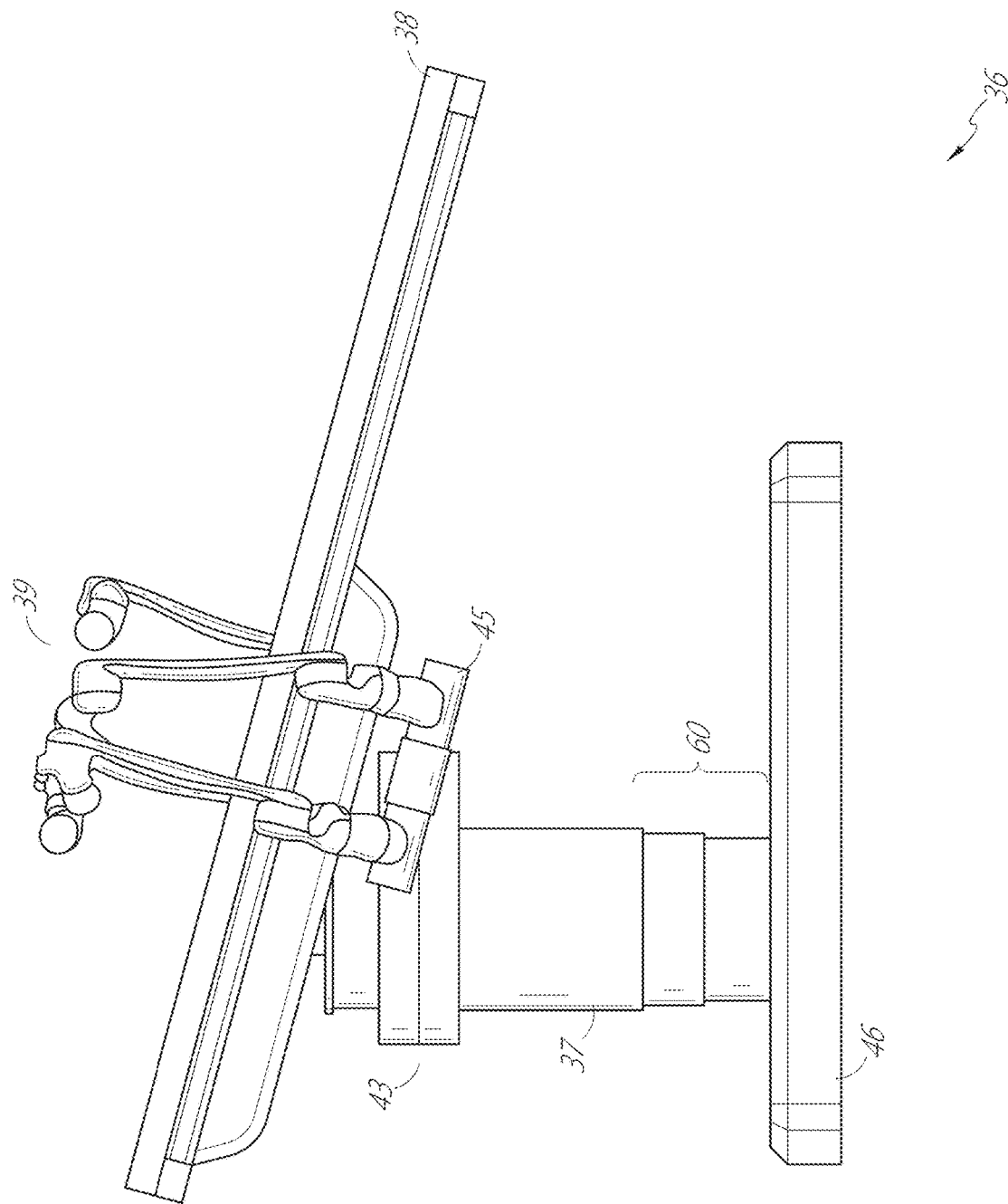
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
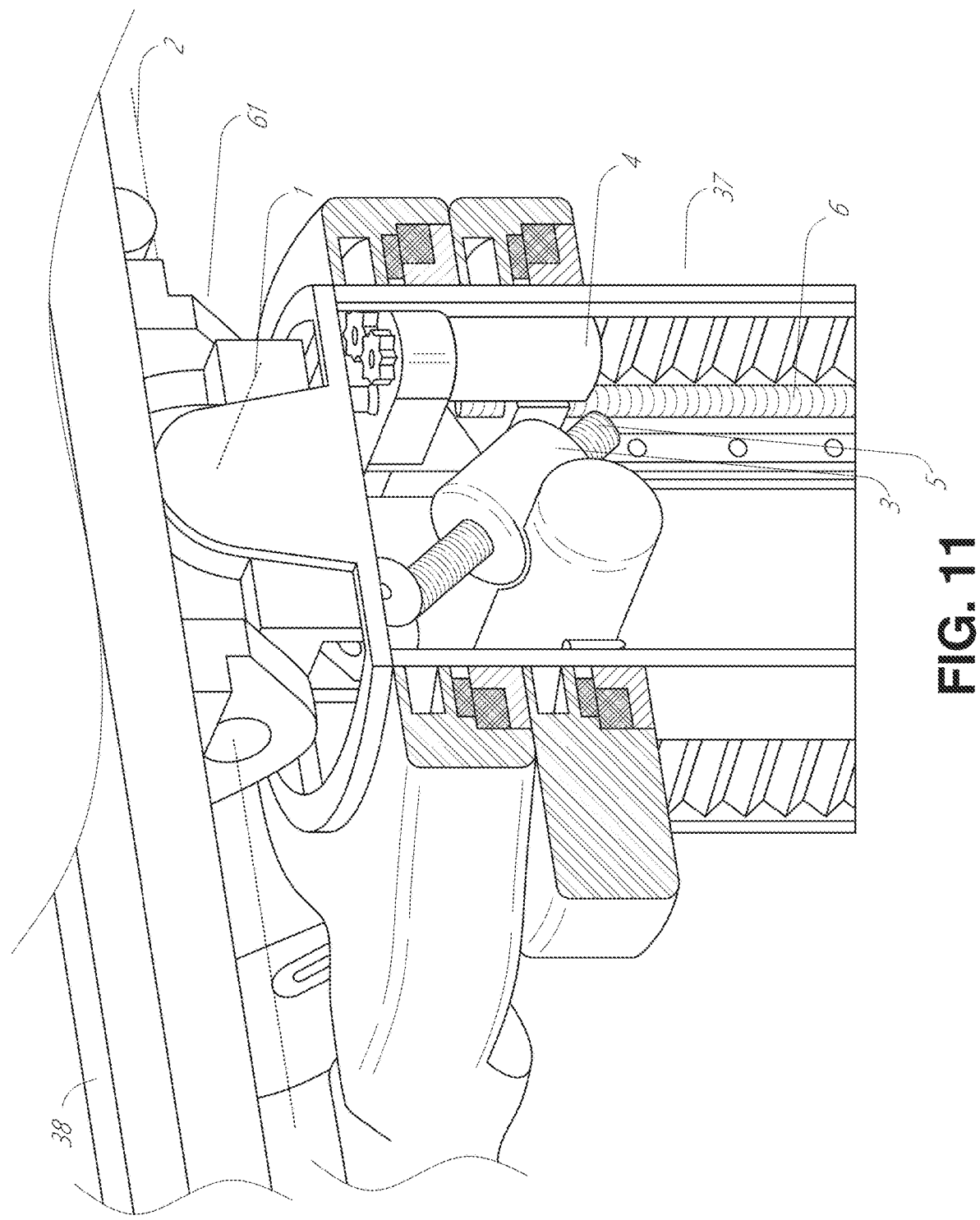
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
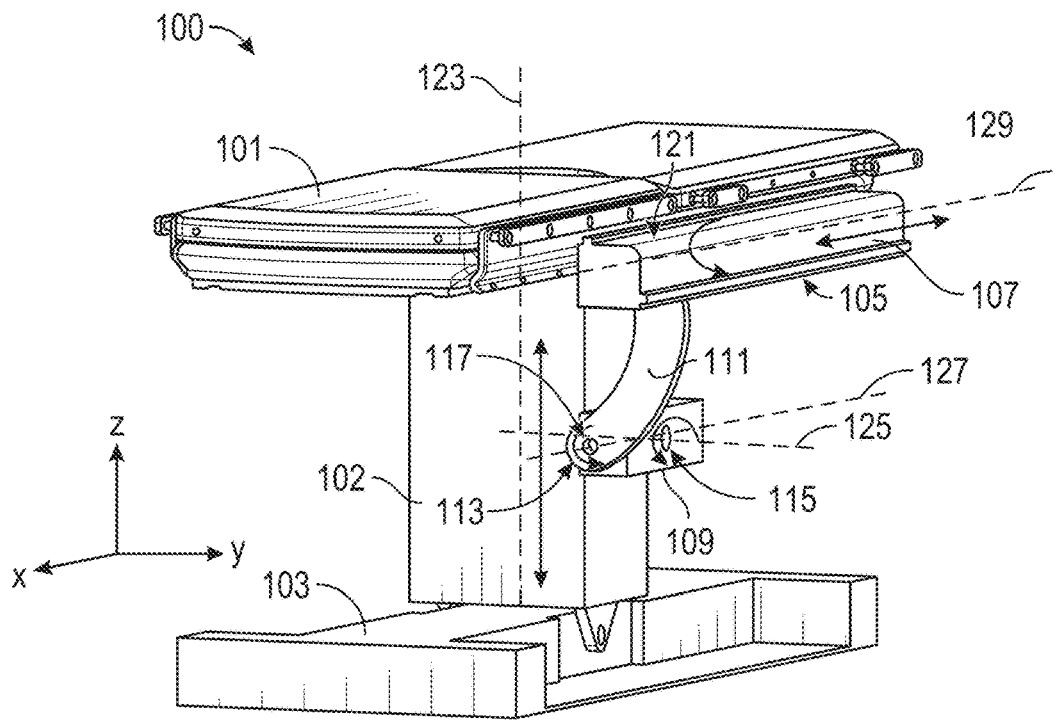
FIG. 12 illustrates an alternative embodiment of a table-based robotic system.
Figure 13:
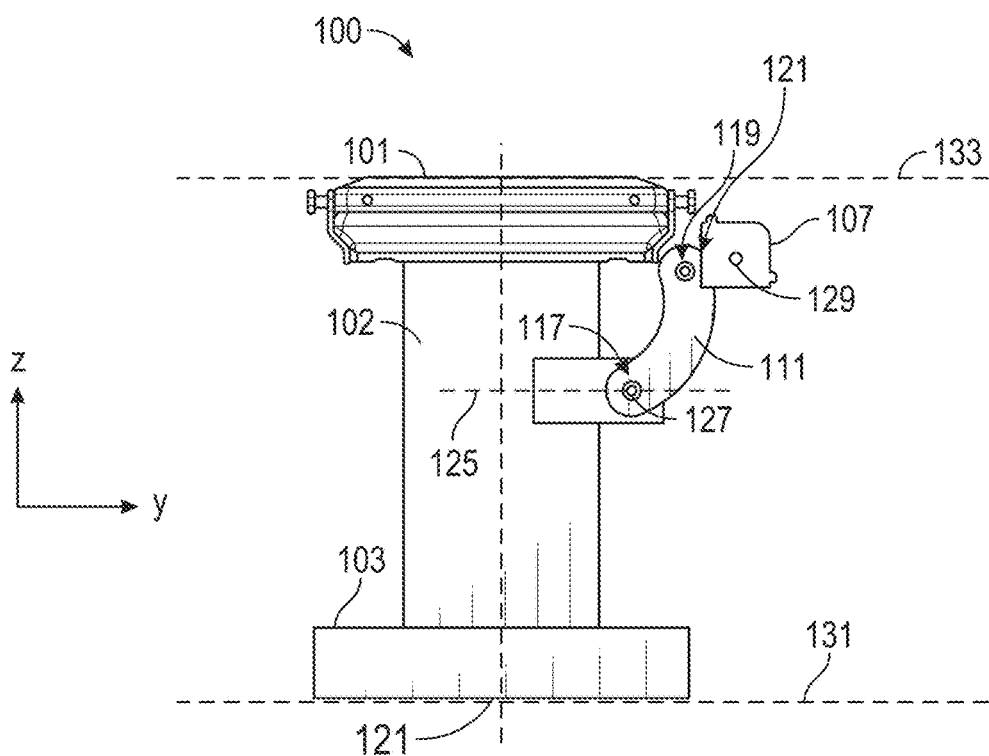
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
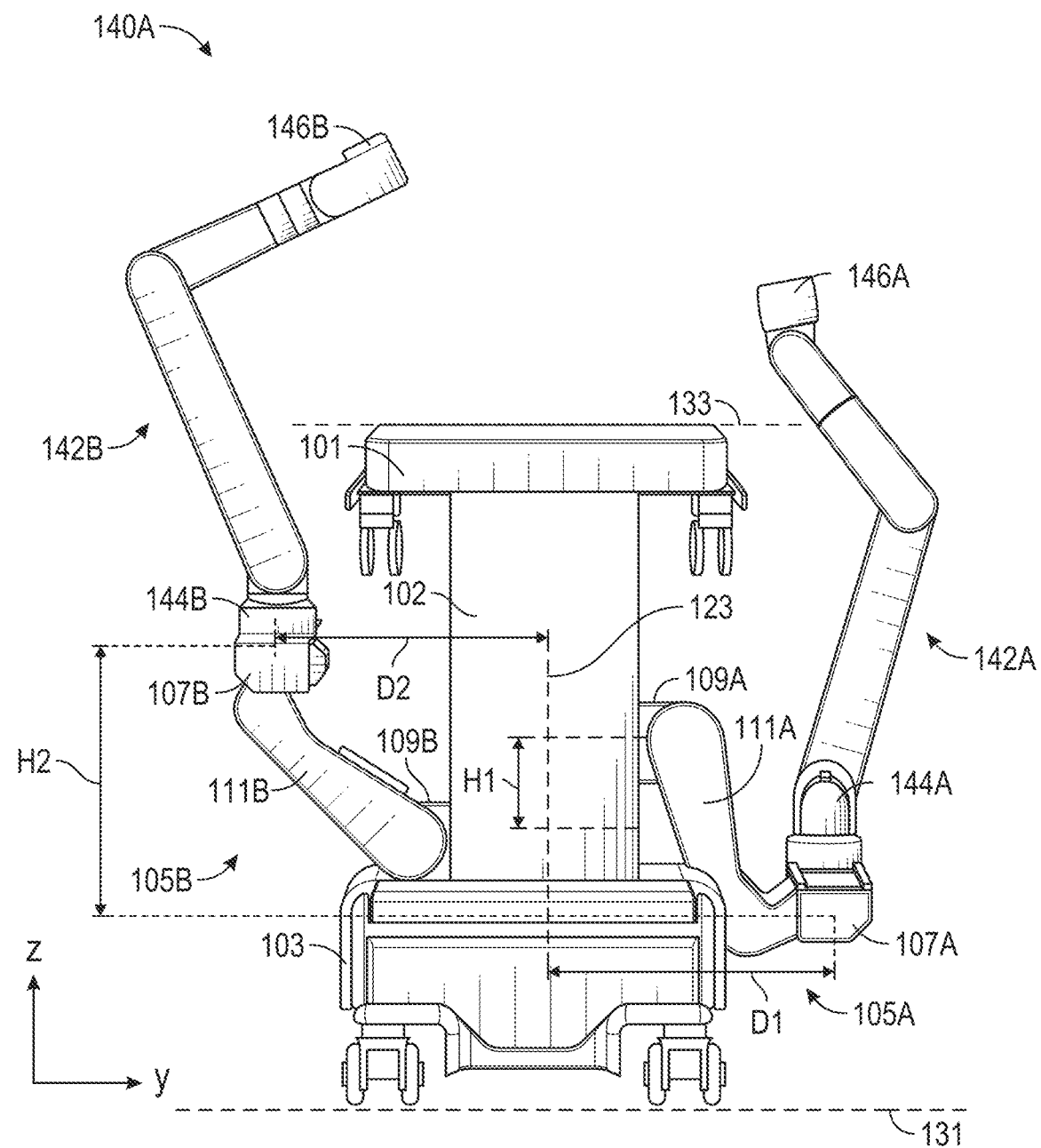
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
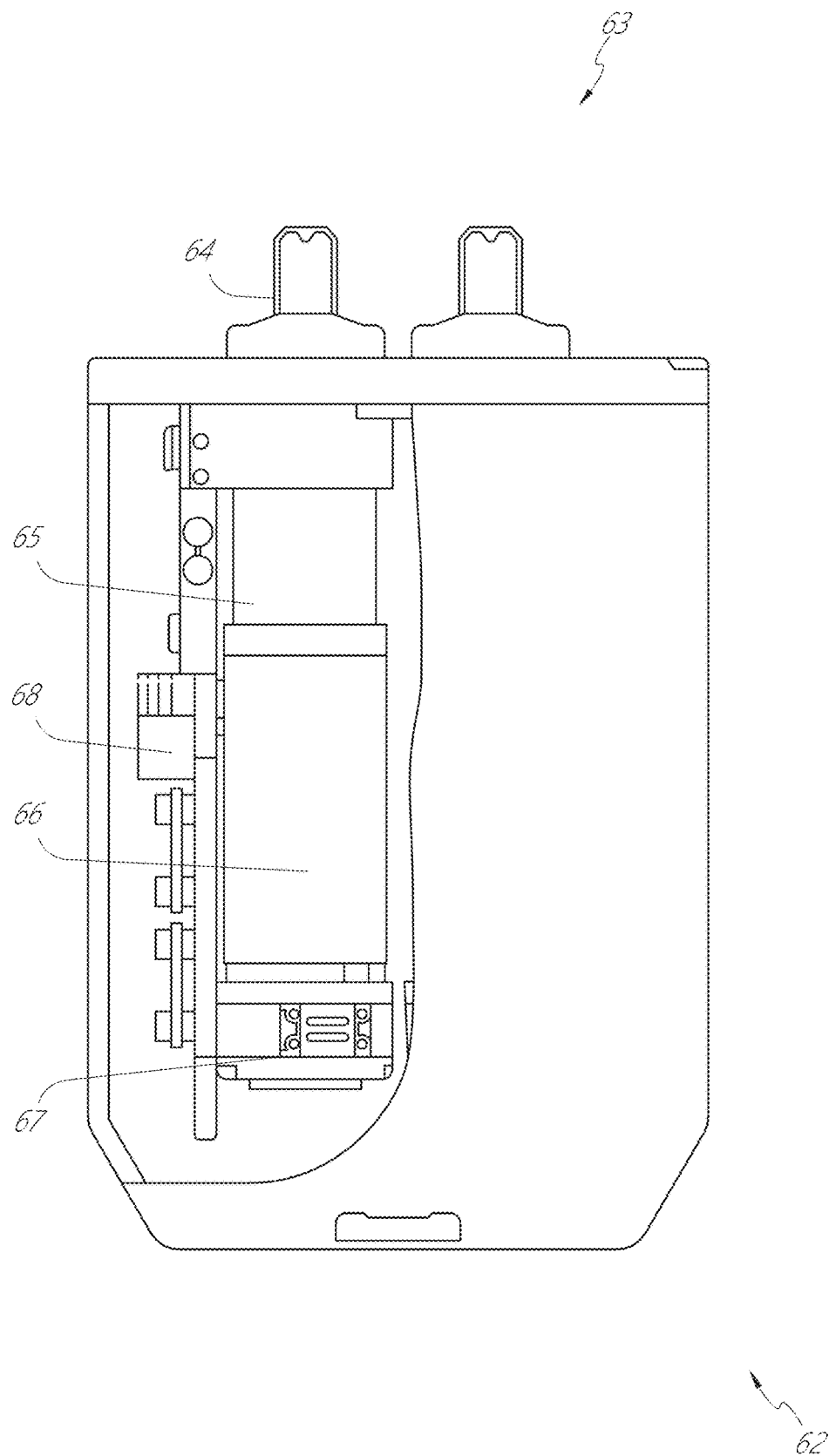
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
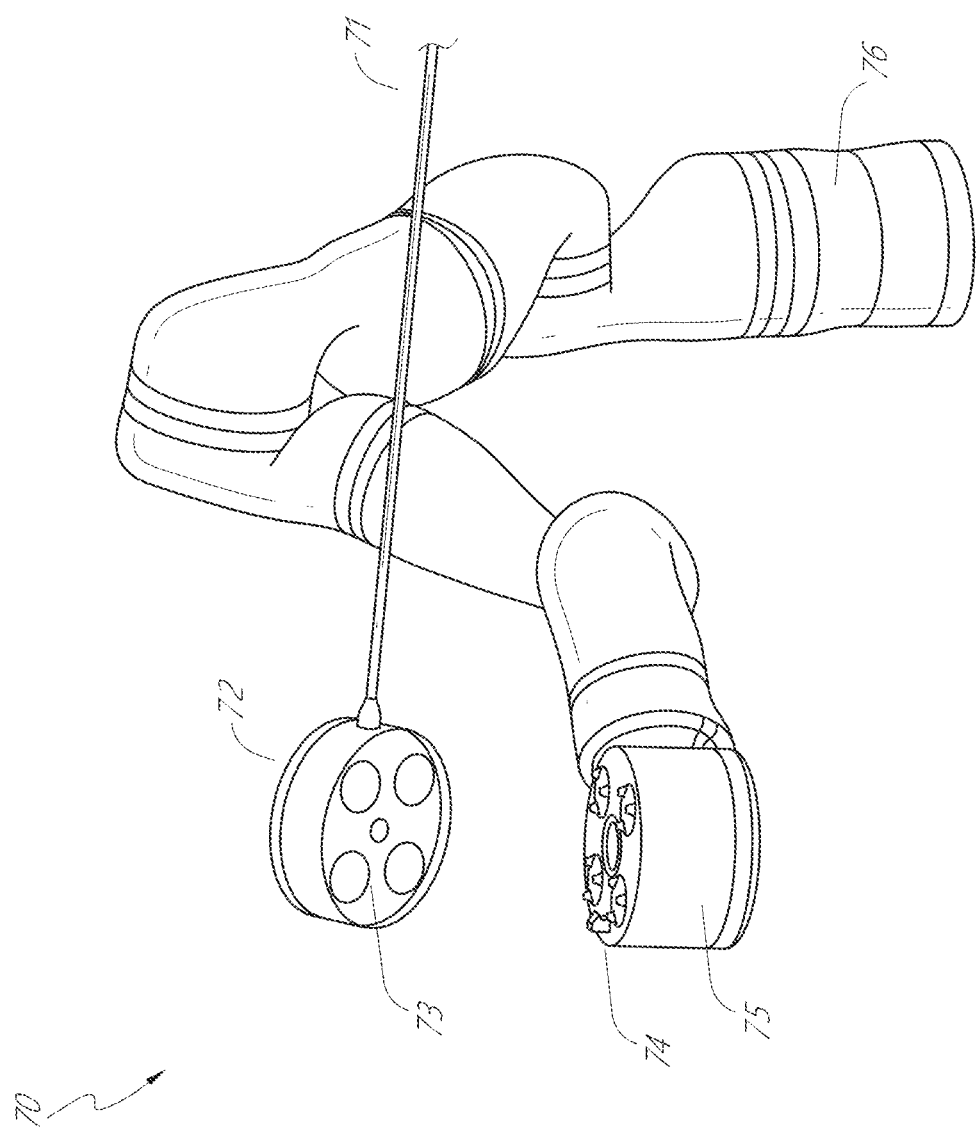
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
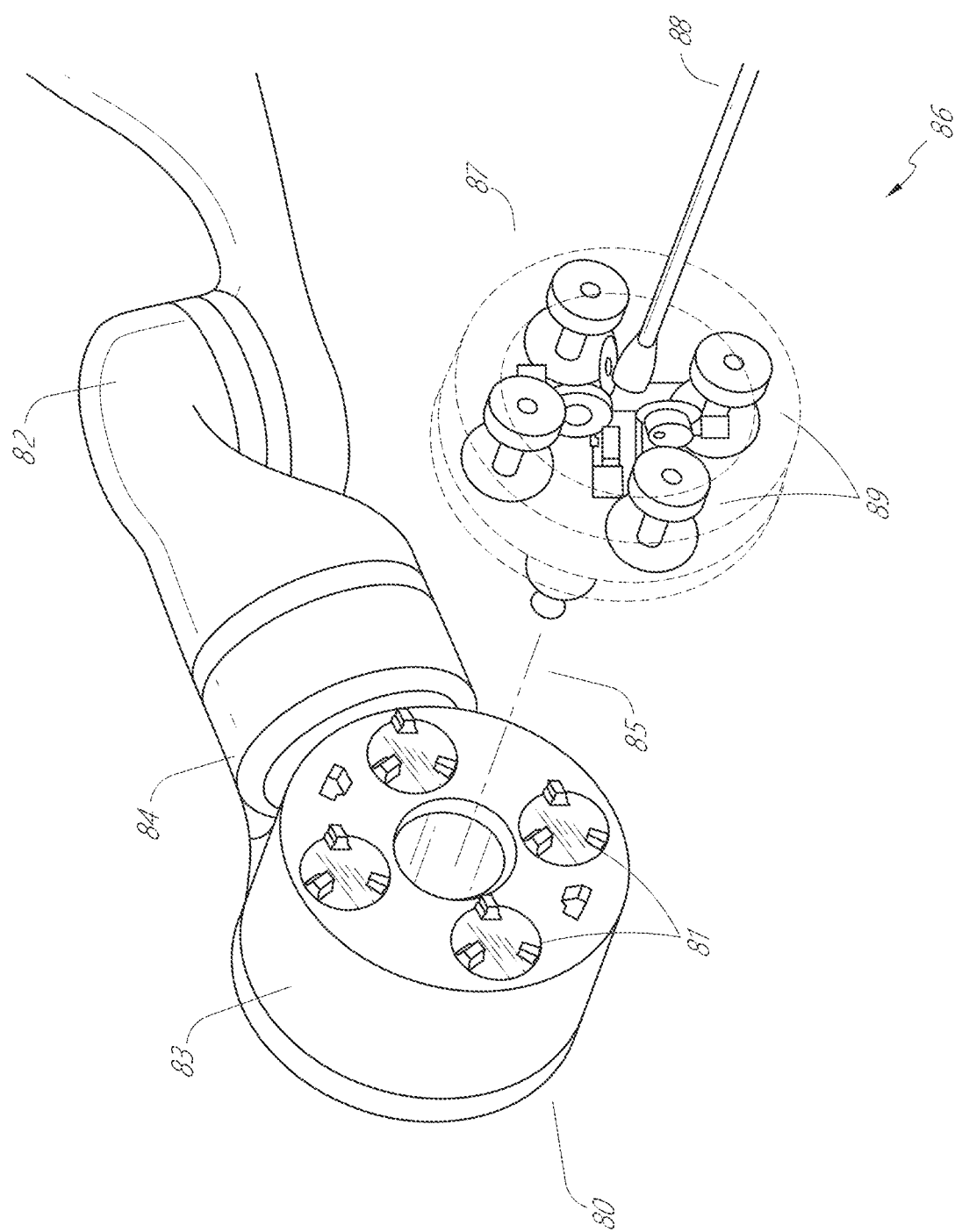
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
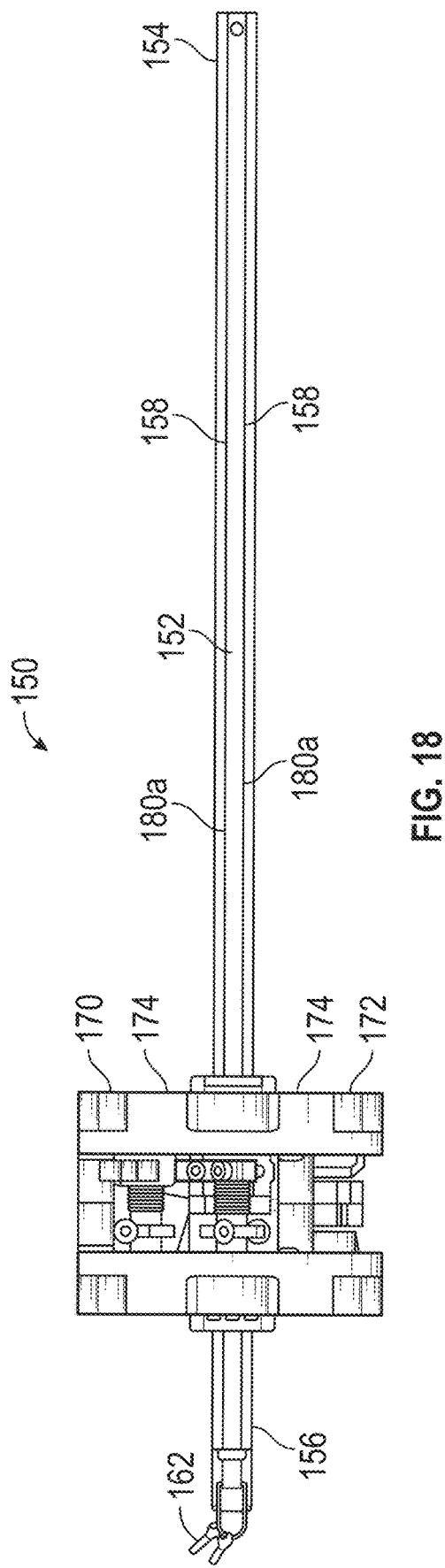
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
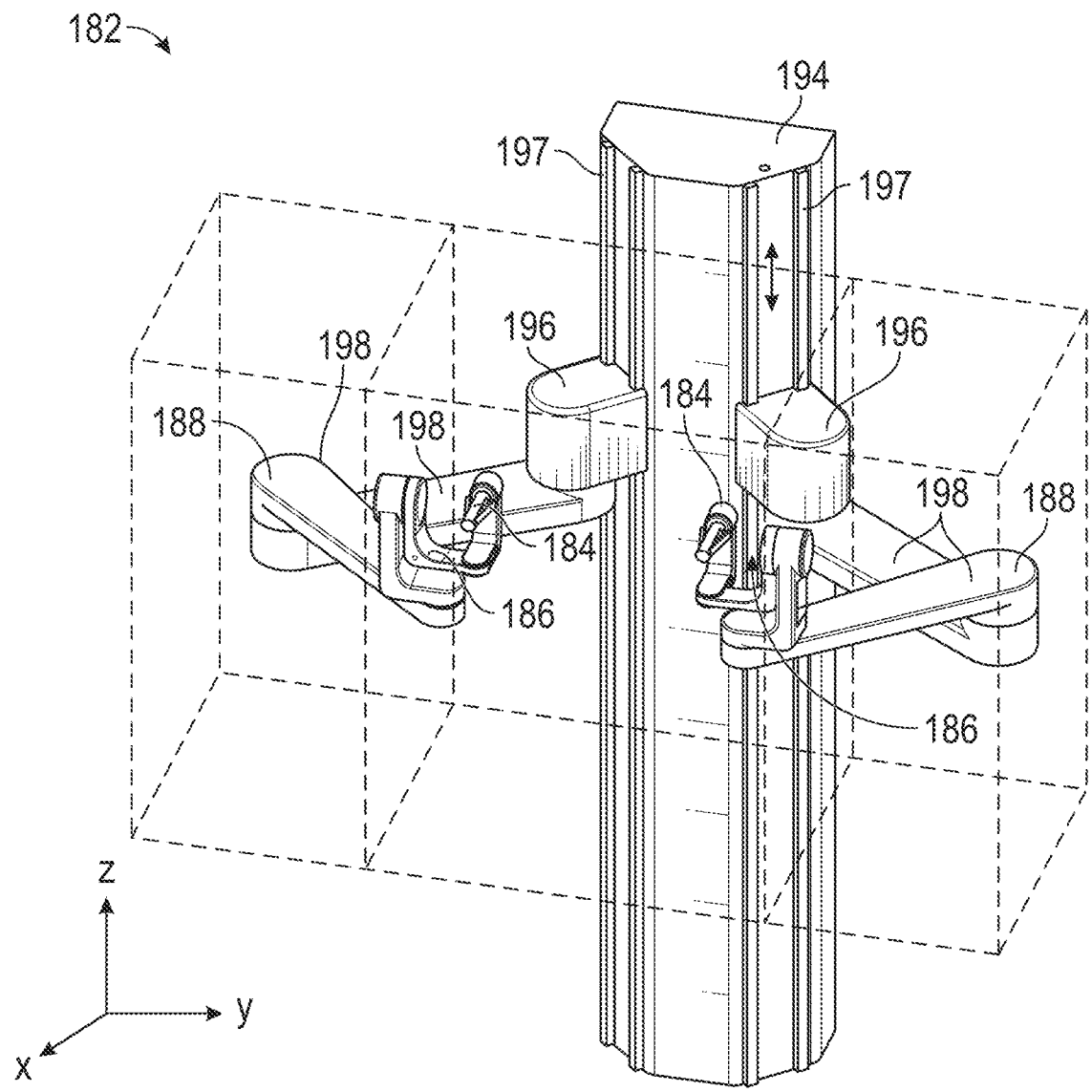
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
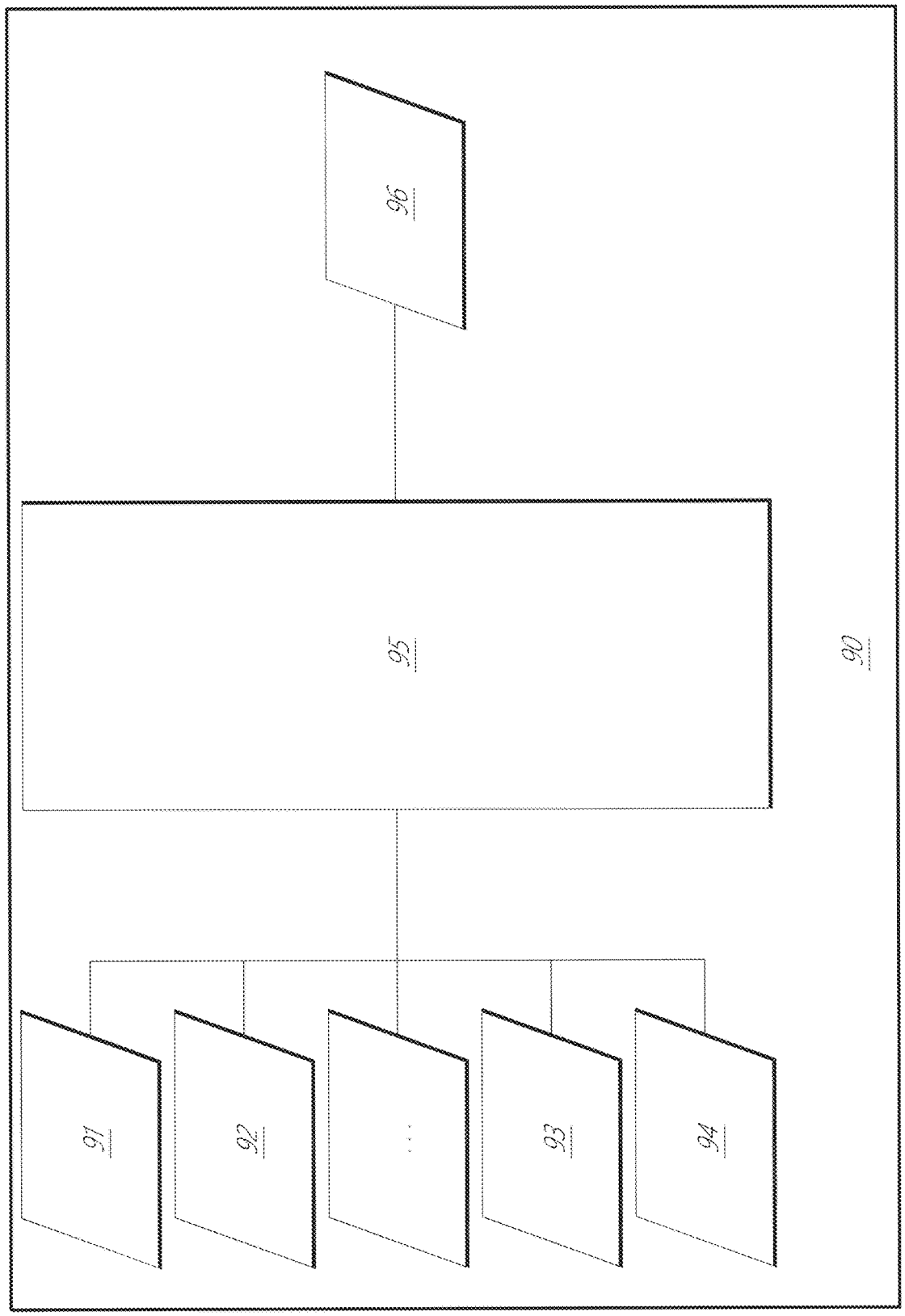
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction to Systems and Methods for Collision Avoidance Using Object Models The present disclosure relates to systems and techniques for collision avoidance using object models. Robotic arms may be used to achieve a desired pose (i.e., position and orientation) of an end effector of a medical tool. In some implementations, the medical tool may include a medical instrument or a camera. In manipulating a robotic arm to achieve the desired end effector pose, there may be a risk that some portion of the robotic arm is moved into a pose that would collide with another nearby object. Examples of objects that may be at risk of collision with the robotic arm(s) may include, but are not limited to, another robotic arm, object(s) associated with the patient (e.g., a patient introducer, the patient himself/herself, etc.), a platform supporting the patient, medical accessories attached to the platform (e.g., IV bags, tubing, padding, EM generators, etc.), objects associated with the bedside staff (e.g., medical accessories operated by the staff, the bedside staff themselves, etc.).

During a medical procedure, robotic arms are expected to be safe enough to operate around other objects in the operating room, including, e.g., humans, medical equipment, and surgical accessories. For example, staff must feel safe coming near a robotic arm to change instruments and drape the system. Staff may interact with one of the robotic arms mid-procedure while other robotic arms in the system are in active use. In another example, an anesthesiologist may set up equipment very near the operating sphere or space (e.g., the volume in which the robotic arms can be positioned) during a procedure. Also, medical accessories (e.g., shoulder supports, foot supports, toboggans, leg boards, arm boards, fences, stirrups, poles, tissue retractors, etc.) may be attached to the platform or otherwise placed within reach of the robotic arms, and such medical accessories may need to be avoided by the robotic arms during a medical procedure.

Certain robotic medical systems can create a model of the robotic system which can be used for collision detection and avoidance. For example, the system can use the internal kinematics of the robotic system to generate a 3D model of the platform, arm bars, robot arms, and instruments. For example, the system may determine the position of each element of the robotic system using encoders at each joint in system, each of which generates a signal indicative of the relative position/orientation of the two links joined by the corresponding joint.

Using this model, the robotic system is able to detect and avoid collisions between hardware components (e.g., robotic arms and medical accessories) based on their current positions. One challenge of the collision detection and avoidance modelling system is that the system may only include models of components that are attached to the system during manufacturing. That is, the size and shape of robotic components of the system can be defined at manufacturing, enabling the system to track the relative positions of each element of the system. However, the robotic arms (or other robotic elements such as the platform) may also collide with other objects in the operating room, including medical accessories. It would be advantageous for the system to detect and avoid collisions between the robotic system and other objects in the operating room. Thus, aspects of this disclosure relate to systems and methods for defining and/or detecting objects or areas that the robotic arms are to avoid, in order to maintain distance(s) between the robotic arms and the objects/areas.

There are a number of different techniques in which the system may be able to define or detect the presence of objects/areas for the robotic arms to avoid. In avoiding the objects, the system may add modelled representations of the objects to the model of the robotic system, enable the system to extend the collision detection and avoidance techniques to the objects added to the model. By adding the modelled object/region to the model of the robotic system, the system can control the robotic arms to provide at least a minimal set of safety features to mitigate the risk of injury or damage to nearby equipment. In addition, the system can also attempt to optimize robotic arm poses to maintain maximal distance from objects within the reach of the robotic arms to avoid situations where the robotic safety actions must be employed (e.g., avoidance actions).

A. Pre-Modeled Object Placement

Figure 21:
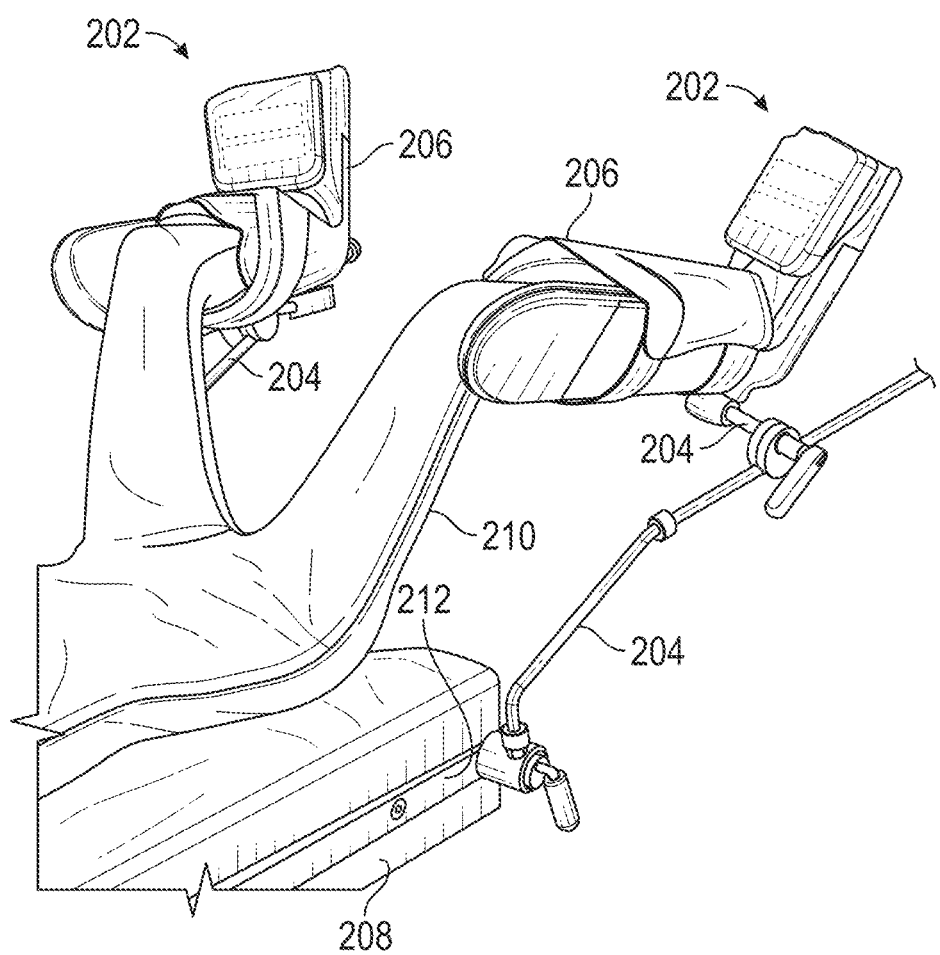
FIG. 21 illustrates an example object that can be attached to a platform in accordance with aspects of this disclosure.

There are a number of defined sets of surgical accessories that can be attached to medical beds, including a platform of the robotic medical systems described herein. These surgical accessories can include stirrups, guard rails, and various accessories that clip onto the bed, such as ventilators. FIG. 21 illustrates an example object that can be attached to a platform in accordance with aspects of this disclosure. Specifically, FIG. 21 illustrates an implementation of a pair of stirrups 202 that can be attached to a rail 212 of a platform 208 configured to support a patient 210. Each stirrup 202 may include one or more adjustable support arms 204 which support the body 206 of the stirrups 202. The stirrups 202 may be configured to support the patient's 210 legs during a medical procedure.

Figure 22:
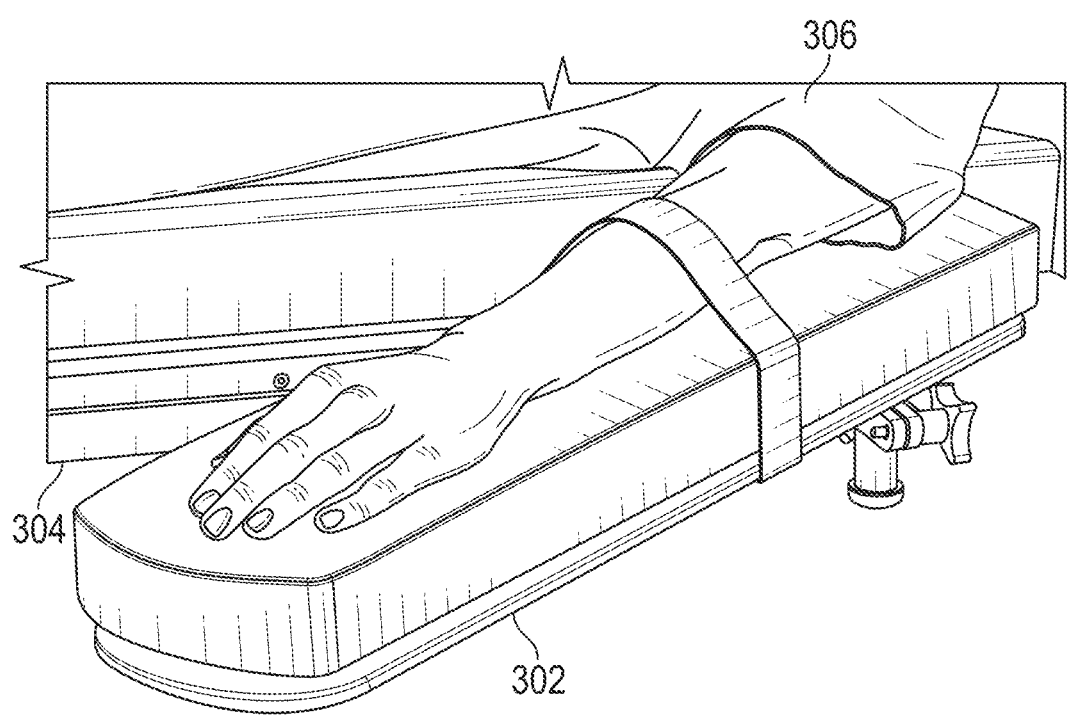
FIG. 22 illustrates another example object that can be attached to a platform in accordance with aspects of this disclosure.

FIG. 22 illustrates another example object that can be attached to a platform in accordance with aspects of this disclosure. The surgical accessory illustrated in FIG. 22 in an arm board 302 that can be attached to a platform 304. Certain procedures may involve attaching a pair of arm boards 302 on opposing sides of the platform 304. The arm boards 302 may be configured to support an arm of a patient 306 during a medical procedure.

Figure 23:
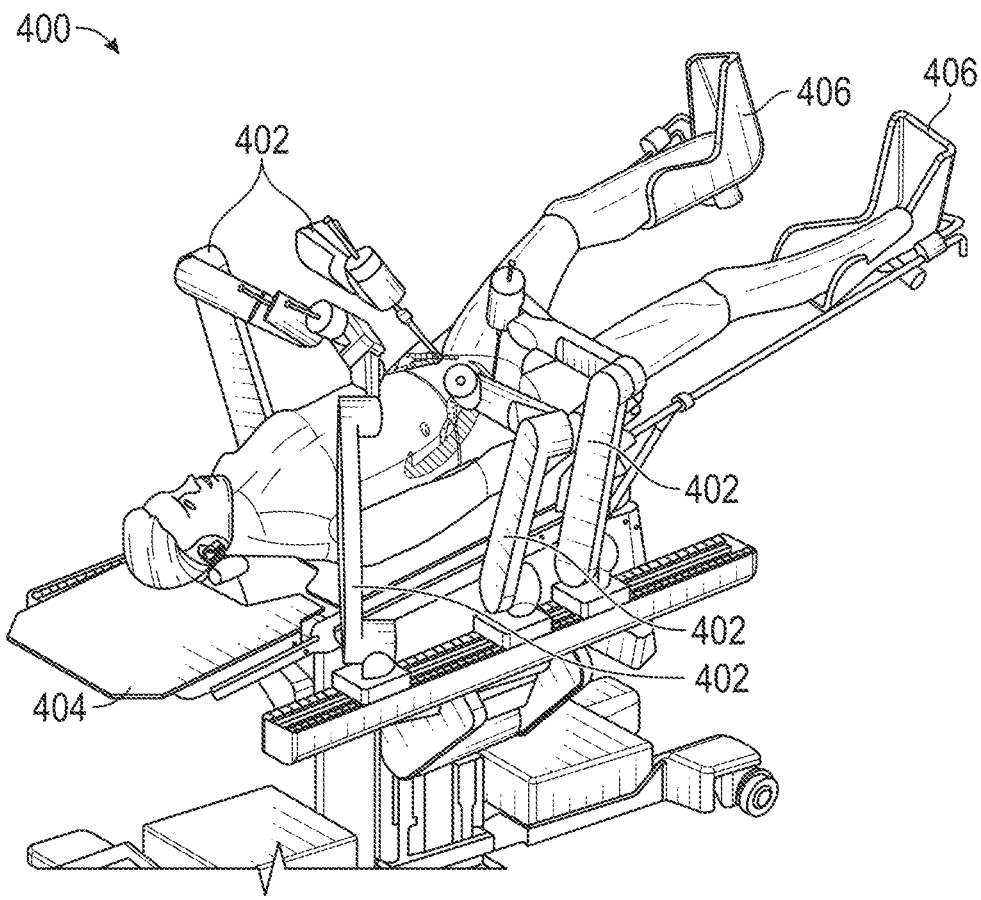
FIG. 23 illustrates an example robotic medical system having medical accessories installed thereon in accordance with aspects of this disclosure.

FIG. 23 illustrates an example robotic medical system 400 having medical accessories installed thereon in accordance with aspects of this disclosure. The illustrated robotic medical system includes a plurality of robotic arms 402 and a platform 404. In the illustrated implementation, a pair of stirrups 406 are attached to the platform 404. As shown in FIG. 23, at least some of the robotic arms 402 may collide with one of the stirrups 406 when moved into certain poses.

There may be challenges for clinicians to manually mitigate collisions between robotic arms 402 or between one of the robotic arms 402 and medical accessories such as the stirrups 406. For example, a clinician may operate the system 400 with his/her head down in a viewer, which may prevent the clinician from seeing the robotic arms 402 outside of the patient's body. Furthermore, each robotic arm 402 may have a plurality of possible positions that achieve the same medical instrument end effector pose due to the inclusion of redundant DoFs in the robotic arm(s) 402. Thus, it may not be immediately apparent to the clinician which robotic arm 402 motions outside of the body will result from the commanded end effector motions inside of the body. The result is that robotic arms 402 may collide with each other or with medical accessories (e.g., the stirrups 406) without the clinician being able to predict the collision.

Thus, in some implementations, the robotic medical system 400 can advantageously model the robotic arms and medical accessories and prevent collisions between the robotic arms and the medical accessories. For example, the system may prevent the collision by preventing movement of the robotic arm towards the medical accessories. The system may also prevent the collision by moving the robotic arm in null space. Additional details regarding detection and avoiding robotic arm collisions are provided in U.S. Provisional Patent Application No. 62/906,612, titled "SYSTEMS AND METHODS FOR COLLISION DETECTION AND AVOIDANCE" filed on Sep. 26, 2019, which can be extended to detecting and avoiding collisions between the robotic arm and medical accessories as described herein.

Some attachable surgical accessories are rigid. For such rigid objects that do not move during a procedure, the system can update the model of the robotic medical system to include a representation of the rigid object(s) using predefined models for the rigid objects. The predefined models can be stored in memory of the robotic system. Examples of predefined models include, but are not limited to: a 3D representation of the rigid object (e.g., a CAD-based model), an approximated model using geometric forms (e.g., capsules, cylinders, rectangles, etc.), etc. In certain implementations, the robotic medical system can receive input from a user (e.g., via a console or master controller such as console 31 of FIG. 1 and/or controller 182 of FIG. 19) that is indicative of one or more objects are within reach of the one or more robotic arms and allow the user to position the predefined model(s) in the system model. For example, the system can receive input from the user that allows the user to select the equipment type that has been pre-modeled and specify the mounting location (e.g., on a rail of the platform) on a computer generated image. The console can be configured to receive input commanding motion of the robotic arms for use during a medical procedure.

Figure 24A:
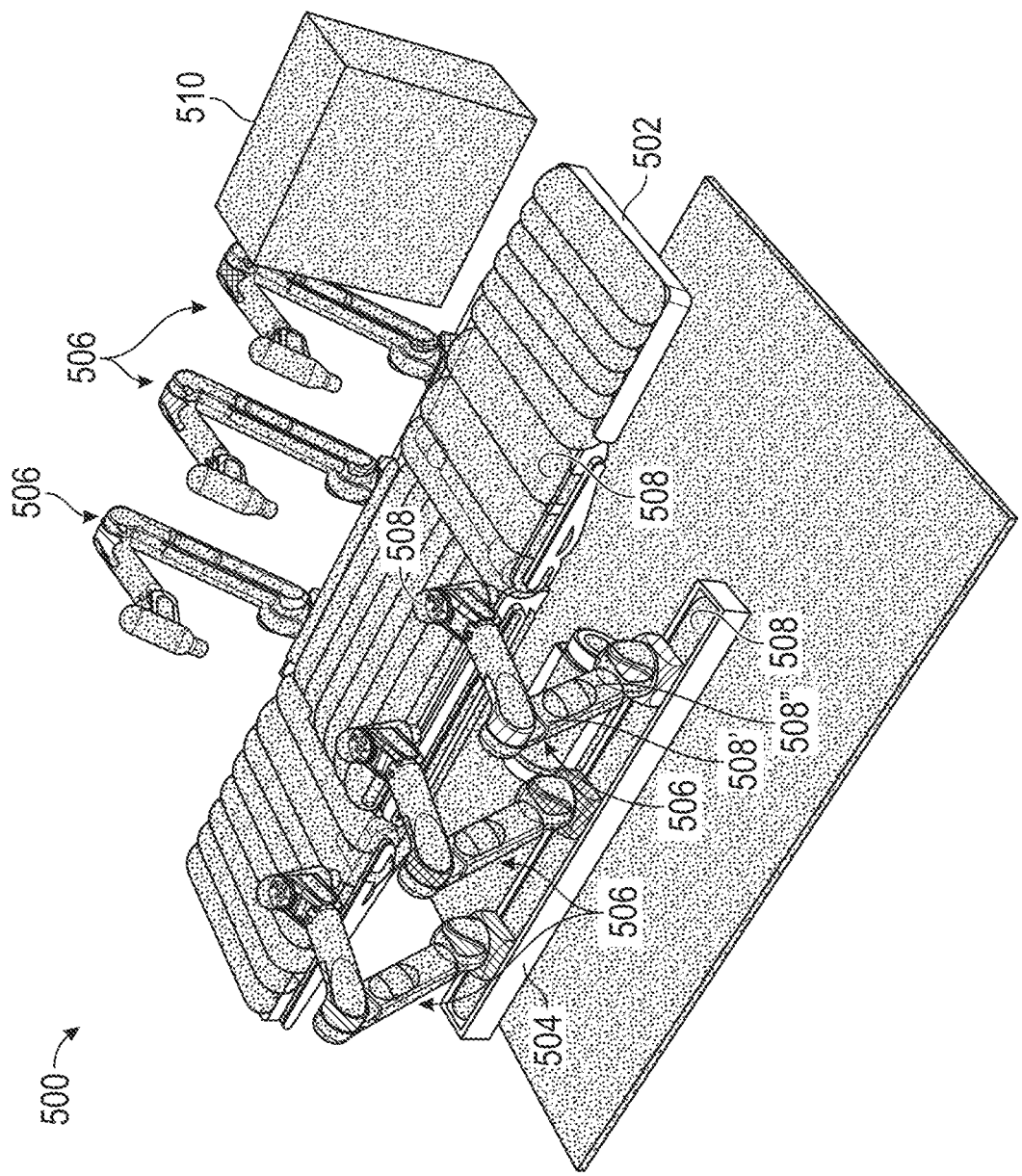
FIGS. 24A and 24B illustrate a model of a robotic system approximated using a geometric form in accordance with aspects of this disclosure.
Figure 24B:
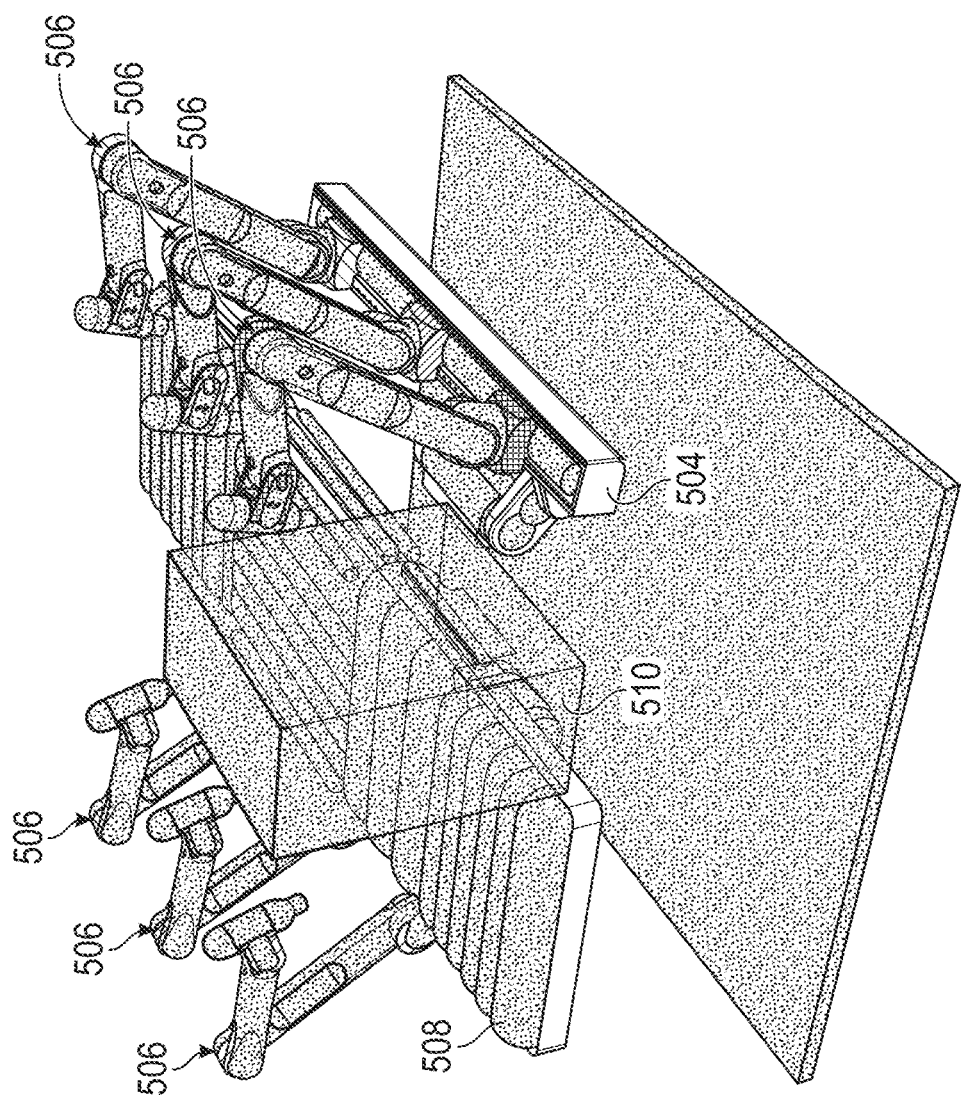

FIGS. 24A and 24B illustrate a model of a robotic system approximated using a geometric form in accordance with aspects of this disclosure. In particular, FIG. 24A illustrates a first perspective view of the robotic system model 500 and FIG. 24B illustrates a second perspective view of the robotic system model 500. The model 500 includes a plurality of links that model a platform 502, adjustable arm support(s) 504, and a plurality of robotic arms 506. The model 500 may include additional links that model other components of a robotic system which are not illustrated in detail, such as one or more medical instruments, a base, etc. In some implementations, the model 500 is formed based on a series of rigid transformations (e.g., based on the relative size of each link) for each of the links 502-506 and the distance or angle between each of the links 502-506 (e.g., the joint angle(s) read from the encoders). The model 500 can be generated using, for example, a CAD model drawn for each link 502-506 with software used to rotate the links 502-506 so that the links 502-506 line up with the corresponding joint angles. The computer generated image of the model 500 may look very much like the actual hardware of the robotic system at a given point in time. In some implementations, the model 500 maintained by the robotic system may not be stored in a human-viewable format.

In some implementations, the system may generate a human-viewable model and provide the model to be viewed by a clinician (e.g., in the viewer of the clinician console or the clinician assistant console). In other implementations, the model is not viewable by a clinician, but can be running behind the scenes in the system. The clinician may be capable of pulling up a view of the model when the model is hidden from view.

Using the model 500 of the robotic system, the system may be able to perform certain actions based on the current configuration of the robotic system. Advantageously, one action that the system can perform is detecting when two pieces of hardware are about to collide and prevent the pieces of hardware from colliding.

One aspect of providing for collision detection and avoidance using a model may involve the system determining how close each link is to colliding with every other link in the system. There are a number of different techniques that can be used to determine how close each link is to each other link. In one implementation, the system can use the CAD model directly to determine these distances. In another implementation, the system can generate an approximation of the model based on the CAD model which can be used to speed up computation of the distances between links. One technique for approximating the CAD model involves generating an approximation for each link using a geometric form approximation for each link. In one implementation, the links may be approximated as "capsules." In other implementations, geometric form(s) used in the approximation can include using cylinders, rectangles, cuboids, etc. The system can efficiently determine a minimal distance between each capsule in the approximated model using the geometric approximations.

Each link 502-506 of the model 500 can be approximated using one or more capsules 508 to simplify the calculation of the distances between the links. For example, two of the links forming a robotic arm 502 can be modelled using two capsules 508' and 508". The capsules 508' and 508" overlap and can be moved longitudinally with respect to each other in accordance with a change in the distance between the corresponding links, which is measured using an encoder arranged between the links. Similarly, the platform 502 can be modelled using a plurality of capsules 508, which can overlap and may be able to move with respect to each other to model movement of the platform 508.

As is described in detail below, the system can use the model 500 to detect and/or avoid collisions between a robotic arm 502 and another object in the workspace. In order to detect such a collision, the system can update the model 500 to include a model of the object 510. The system can then determine whether a given pose of a robotic arm would result in a collision with the object model 510, which can be used to prevent the collision from occurring. Certain aspects of this disclosure relate to systems and methods which can be used to update the system model 500 to include one or more object models 510 for use in collision detection and avoidance.

Figure 25:
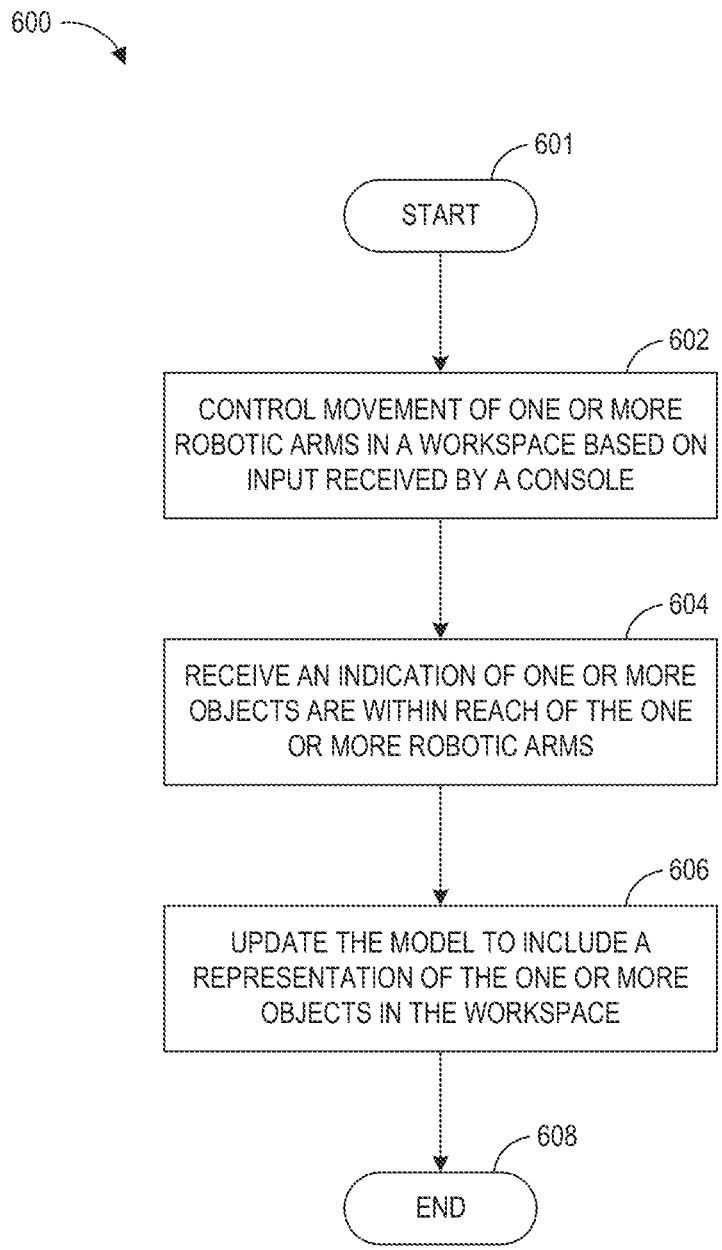
FIG. 25 is a flowchart illustrating an example method operable by a robotic system, or component(s) thereof, for updating a model of a robotic medical system to include a representation of one or more objects in a workspace in accordance with aspects of this disclosure.

FIG. 25 is a flowchart illustrating an example method operable by a robotic system, or component(s) thereof, for updating a model of a robotic medical system to include a representation of one or more objects in a workspace in accordance with aspects of this disclosure. For example, certain steps of method 600 illustrated in FIG. 25 may be performed by processor(s) and/or other component(s) of a medical robotic system (e.g., robotically-enabled system 10) or associated system(s). For convenience, the method 600 is described as performed by the "system" in connection with the description of the method 600.

The method 600 begins at block 601. At block 602, the system controls movement of one or more robotic arms in a workspace based on input received by a console. For example, with reference to FIG. 23, the system 400 can control the robotic arms 402 within a workspace in order to perform a medical procedure on a patient. In some implementations, the workspace may correspond to the operating room in which the robotic medical system is located. The workspace may include the 3D volume reachable by the robotic arms 402. The console from which the input is receive may include, for example, a controller such as the controller 182 of FIG. 19.

At block 604, the system receives an indication of one or more objects are within reach of the one or more robotic arms. As discussed in greater detail in the implementations provided below, the system may receive an input from a user via a console (e.g., via a console such as console 31 of FIG. 1) that is indicative of the one or more objects, or the system may directly detect the presence of the one or more objects using sensor(s). At block 606, the system updates the model to include a representation of the one or more objects in the workspace. For example, as shown in FIGS. 24A and 24B, the system may include a model of a medical accessory 510 located within the workspace. The system can use the medical accessory model 510 in order to detect and/or avoid collisions and thereby prevent collisions between the medical accessory and the robotic arms. The method 600 ends at block 608.

In implementations where the system receives input indicative of the one or more objects, the system may display a computer generated image of the model 500 and receive the input from a user via the console. The input can include commands to move a model of a medical accessory 510 to a location with respect to the model 500 that substantially corresponds to the medical accessory's physical location in the operating room. For example, in one implementation, the user can drag and drop a representation of a pre-modeled object 510 into the 3D model. Although FIGS. 24A and 24B illustrate the capsule-based model 500, in other implementations, the system may hide the simplified model (e.g., the capsules) and present a more representative 3D model to the user, such as an image of the robotic medical system 400 illustrated in FIG. 23.

Based on the received user input, the system can update the model 500 to include a representation of the added medical accessory 510. The system can use the medical accessory model 510 to detect and/or avoid collisions between any link within the model 500 and the medical accessory. Depending on the implementation, the medical accessory model 510 can be a representation that closely matches the geometry of the medical accessory or can be a geometrical representation of the pre-modeled object (e.g., a capsule, rectangle, etc.). If the system lacks a pre-modeled representation of the medical accessory 510, the user can create a new volume that encompasses the medical accessory (e.g., a box) and place the volume within the model 500.

B. Advanced Sensors for Pre-Modeled Objects

Although a robotic surgical medical can allow a user to add pre-modeled objects to a model of the robotic medical system, aspects of this disclosure also relate to implementations in which the robotic medical system can automatically update the model of the robotic medical system by adding pre-modeled objects of medical accessories to the model. For example, with reference to FIG. 21, the robotic medical system 200 can further include one or more sensor(s) (not illustrated) configured to detect when one or more objects (e.g., medical accessories) are positioned within the reach of the system's the robotic arms. In some implementations, the sensor(s) can be located on or near the rail 212 of the platform 208 in order to detect medical accessories that are attachable to the rail 212. In other implementations, the sensor(s) can be located on one or more arm supports (e.g., see the arm support 302 of FIG. 22).

Returning to FIG. 21, the sensor(s) can be configured to detect the presence of the stirrups 202 when the stirrups are attached to the rail 212. In response to a signal from the sensor(s), the system can update the model of the robotic medical system to include a modeled representation of the stirrups, for example, by including a medical accessory model (e.g., the medical accessory model 510) in a position indicated by the signal received form the sensor(s). The robotic medical system can then use the updated model to detect and/or avoid collisions of the robotic arm(s) with the added medical accessories.

As one example, certain medical procedures, such as a laparoscopic procedure, can involve the use of bed-rail mounted surgical accessories. These accessories may include range from patient positioning devices (like stirrups) to IV poles to liver retractors. Many of these bed-rail mounted accessories take up the same volume that is entered by our robotic arms (e.g., the stirrups 406 in the robotic medical system 400 of FIG. 23). Thus, the robotic medical system 400 can include one or more sensors that can detect when accessories are attached to the platform 404.

In some implementations, the sensors may simply detect that a medical accessory has been attached to rails (not illustrated) on the platform 404. In these implementations, the user may be able to modify the shape and/or size of a model of a generic medical accessory to better match the space occupied by the attached medical accessory. However, in other embodiments, the sensors can detect the type of attached accessory. For example, the sensor may include radio-frequency identification (RFID) sensors configured to read an RFID tag included on the medical accessory attached to the platform 404. Thus, each accessory can include an RFID tag that defines the accessory type, and optionally, the size, shape, and/or current configuration of the accessory. The robotic medical system 400 can use the information read from the RFID tag(s) of any accessories attached to the platform 404 to update the model of the robotic medical system 400. In other implementations, the sensor(s) can include optical sensors (e.g., that read reflective or other visual information from the medical accessories), magnetic sensors, inductive sensors, etc.

Implementations that include sensors to automatically update the model of the robotic medical system have advantages over systems which involve manually updating the model, since the user is not required to "teach" the robotic medical system where keep-out zones are and the accessories do not need to be placed so far away from the robotic arm workspace as to reduce the likelihood of collisions.

C. Keep-Out Zones for Non Pre-Modeled Objects

Aspects of this disclosure also relate to systems and methods for automatically updating a robotic medical system model to include objects that are non-rigid and/or not pre-modeled. For example, it can be challenging to design models non-rigid item such as IV bags, tubing, padding, or equipment, that are sufficiently accurate to allow the robotic arms to detect and avoid collisions without creating a large "keep-out zone" for the robotic arms to avoid. The system can allow a user to define one or more 3D regions near the model within which they plan to place the given piece of equipment, thereby creating a keep-out zone. The system would then restrict the robotic arms from enter these keep-out zones, while any equipment would be designed to remain inside.

The medical accessory model 510 of FIGS. 24A and 24B is one example of a keep-out zone that can be placed by a user into the model 500. In the illustrated implementation, the keep-out zone 510 is a rectangular and symmetrical geometric representation—however, in other implementations, the keep-out zone 510 can be a non-rectangular geometric representation (e.g., square, circular, oval, trapezoidal, etc.). In some implementations, the keep-out zone 150 can also be non-symmetrical. In certain implementations, the robotic medical system can include an interface that allows the user to manually create a unique keep-out zone 510 that can be of any shape, including straight and/or curved lines. For example, the interface can allow the user to manually draw a boundary for a keep-out zone via the console. In some implementations, the system may store a database of pre-modeled keep-out zones selectable by the user. The pre-modeled keep-out zones may correspond roughly to the size and/or shape of objects which are commonly placed in the workspace during a medical procedure.

Figure 26:
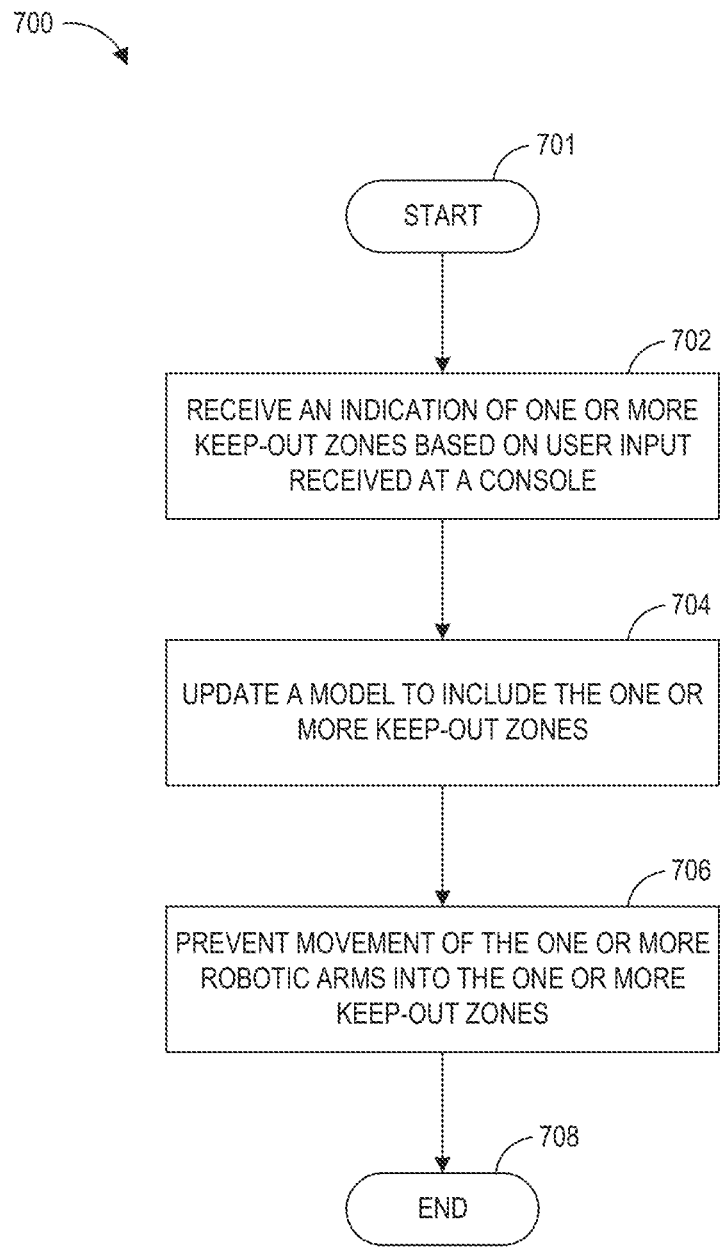
FIG. 26 is a flowchart illustrating an example method operable by a robotic system, or component(s) thereof, for preventing movement of robotic arm(s) using keep-out zone(s) in accordance with aspects of this disclosure.

FIG. 26 is a flowchart illustrating an example method operable by a robotic system, or component(s) thereof, for preventing movement of robotic arm(s) using keep-out zone(s) in accordance with aspects of this disclosure. For example, certain steps of method 700 illustrated in FIG. 26 may be performed by processor(s) and/or other component(s) of a medical robotic system (e.g., robotically-enabled system 10) or associated system(s). For convenience, the method 700 is described as performed by the "system" in connection with the description of the method 700.

The method 700 begins at block 701. At block 702, the system receives an indication of one or more keep-out zones based on user input received at a console. For example, the user may select a keep-out zone having a shape and size corresponding to an object placed in the workspace of the system.

At block 704, the system updates the model to include the one or more keep-out zones. The system may receive addition user input via the console that is indicative of a location in which to place the keep-out zone with respect to the model of the system.

At block 706, the system prevents movement of the one or more robotic arms into the one or more keep-out zones based on the updated model. Thus, the system is able to prevent collisions between the robotic arms and the object by preventing the robotic arms from entering the keep-out zone. The method 700 ends at block 708.

D. Advanced Sensors for Non Pre-Modeled Objects

While the robotic medical system can enable the user to place keep-out zones in the model of the robotic medical system, such keep-out zones may be larger than necessary, thereby limiting the working space for the robotic arms as well as the number of possible poses achievable by the robotic arms. Thus, aspects of this disclosure also relate to implementations of the robotic medical system that include 3D sensors in the operating room or on the robotic medical system that can be used to detect objects around the robotic medical system during operation. The system can use signals received from one or more types of sensors within the environment (e.g., the operating room) to build a dynamic model of the environment and/or of objects not included in the robotic medical system model. Example sensors that can be used to detect objects within the environment include Lidar, image-based sensors, magnetic sensors, RFID, inductive sensors, and EM sensors. When more than one sensor is used, the system can synthesize the signals received from multiple sensors into the dynamic model of an object being sensed and/or the environment.

Figure 27:
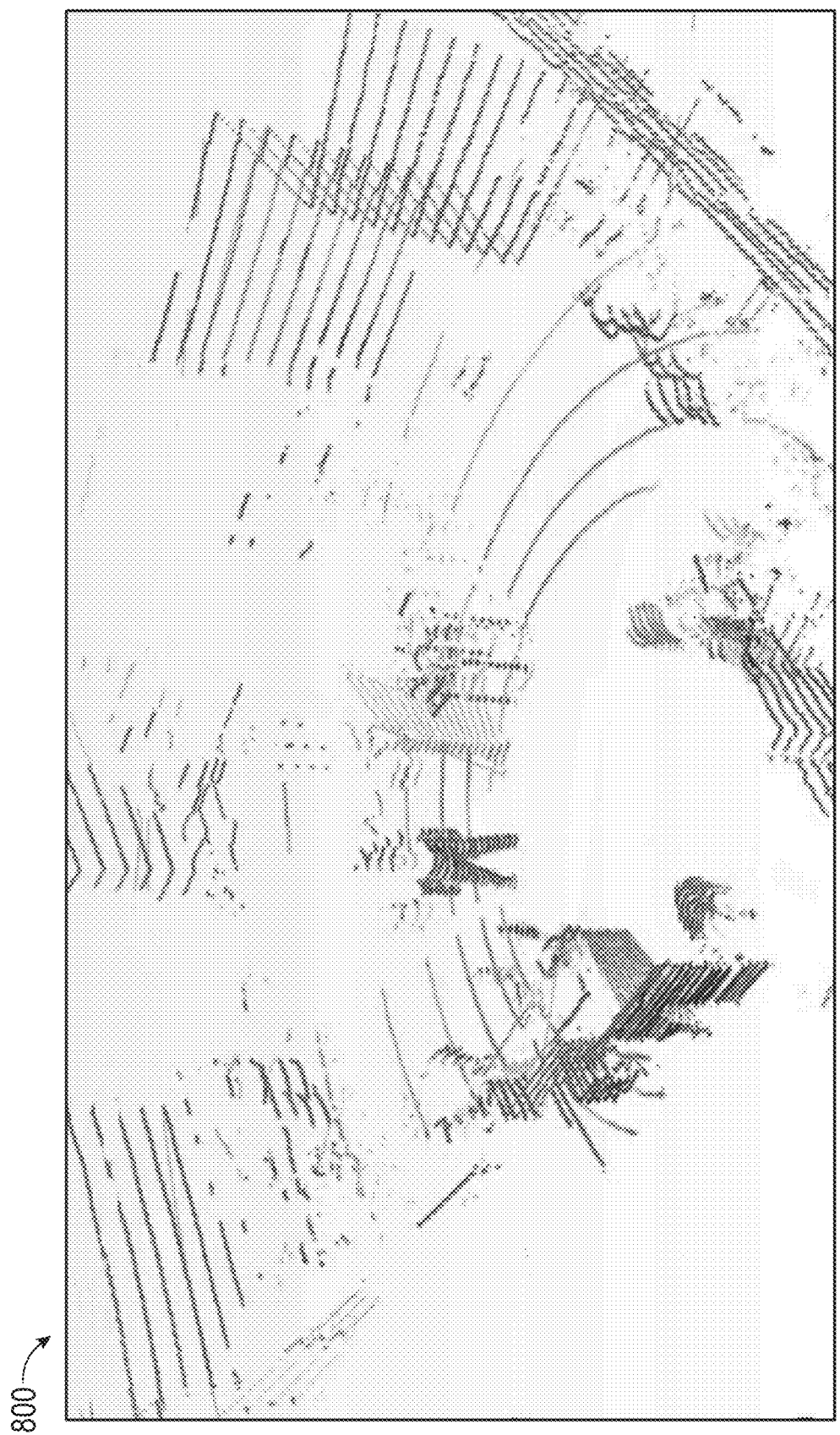
FIG. 27 illustrates an example dynamic model that can be constructed from a light imaging, detection, and ranging (Lidar) sensor in accordance with aspects of this disclosure.

FIG. 27 illustrates an example dynamic model 800 that can be constructed from a Lidar sensor in accordance with aspects of this disclosure. The Lidar sensor can generate the dynamic model 800 using time of flight readings from projected photons. The system can use the dynamic model 800 to detect whether any object(s) are present in the environment and add the detected object(s) to the robotic medical system model.

Figure 28A:
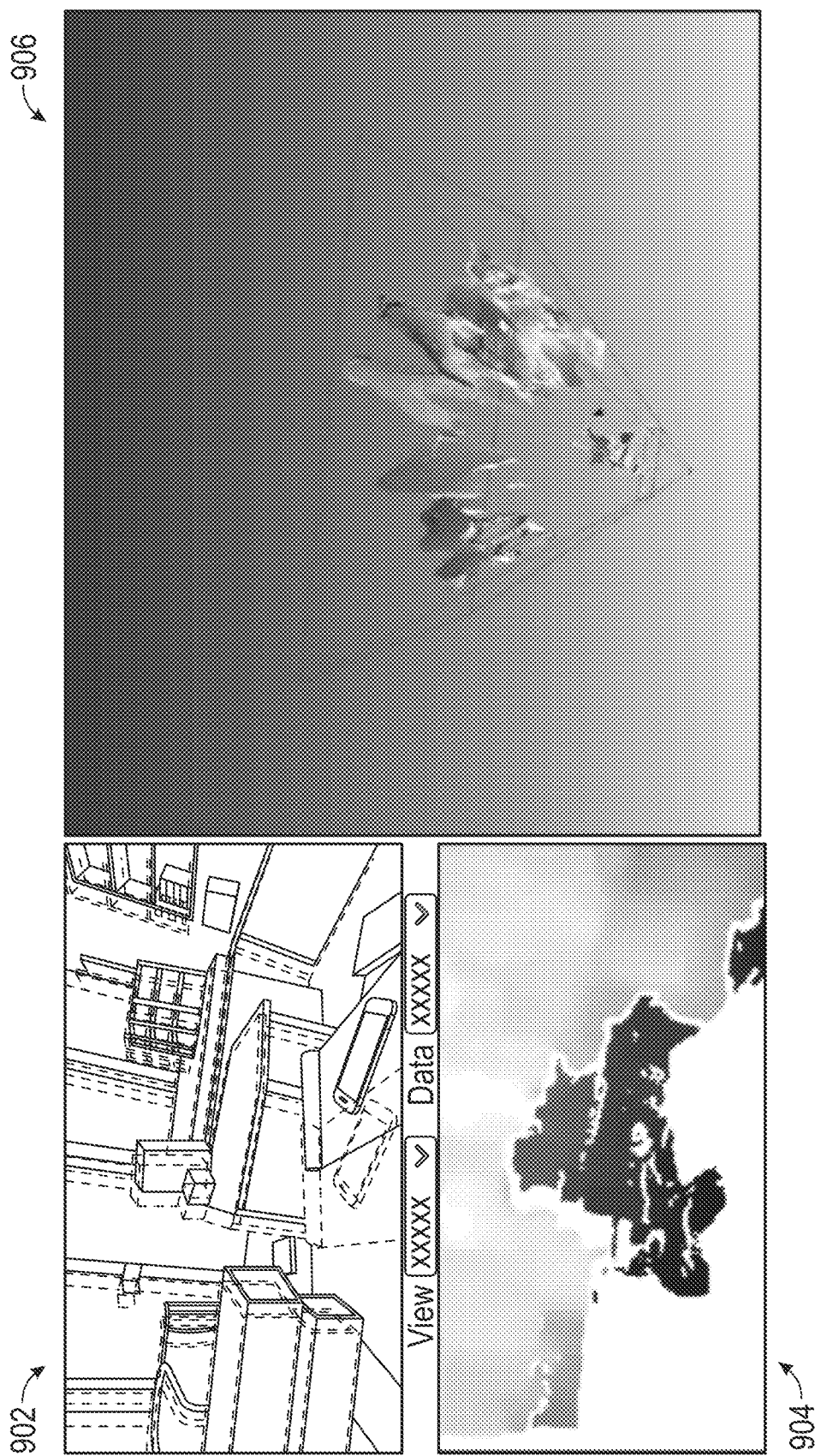
FIGS. 28A and 28B illustrate example dynamic models that can be constructed from a stereo camera in accordance with aspects of this disclosure.
Figure 28B:
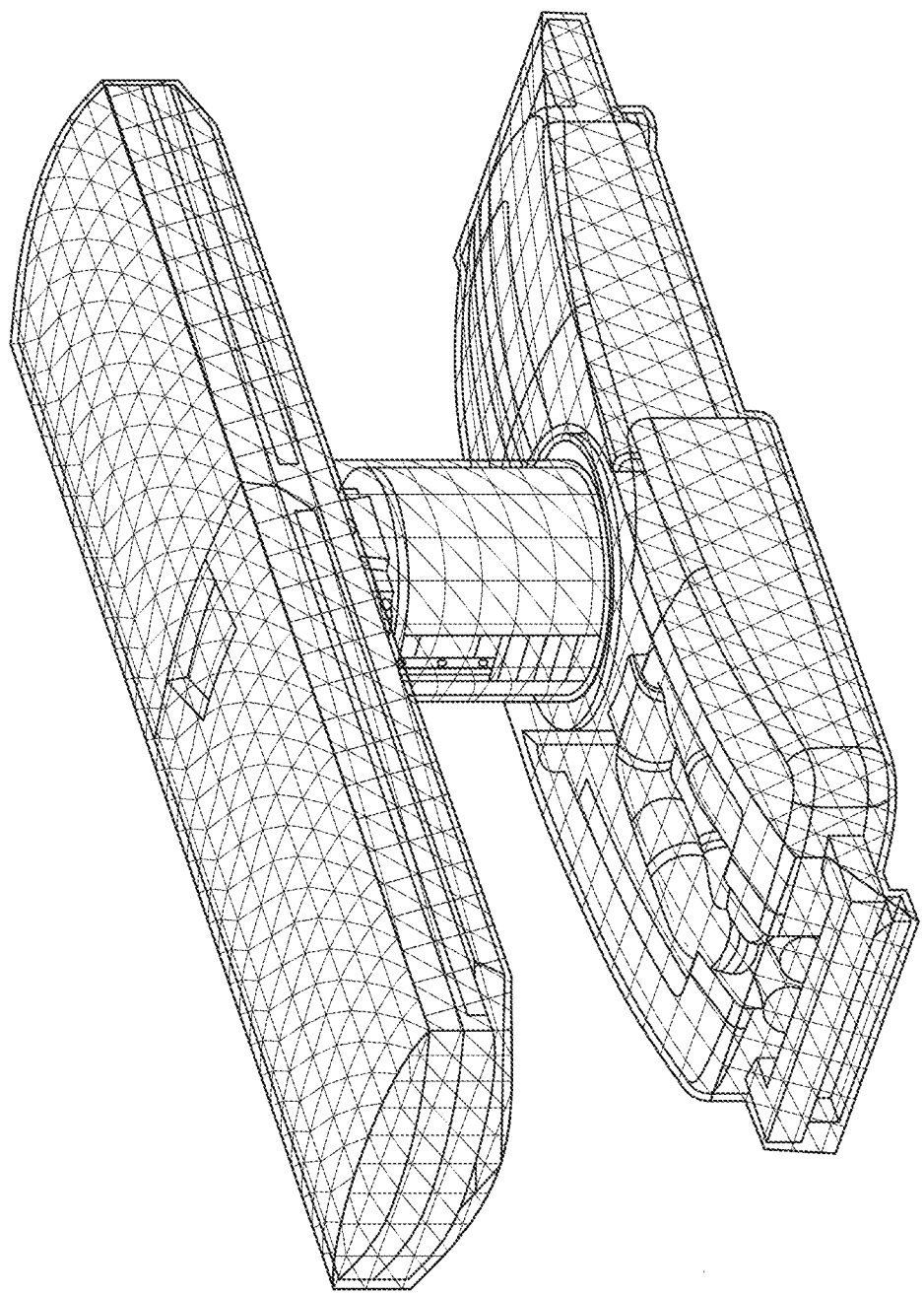

FIGS. 28A and 28B illustrate example dynamic models 906 and 920 that can be constructed from a stereo camera in accordance with aspects of this disclosure. With reference to FIG. 28A, the stereo camera can generate the dynamic model 906 by building a 3D reconstruction from image disparity between the two images captured by the stereo camera. For example, the image 902 illustrates two images captured from a stereo camera superimposed on each other to illustrate the disparity between the two images. Image 904 provides an example reconstructed view from the point of the stereo camera constructed using the image disparity from the superimposed image 902 while image 906 provides an example 3D model constructed using the image disparity from the superimposed image 902.

FIG. 28B illustrates another example image in which a dynamic model 920 including a wire frame 3D model is superimposed on a 2D image captured by a stereo camera. The dynamic model 920 can be generated using the disparity between the two images captured by the stereo camera.

Figure 29B:
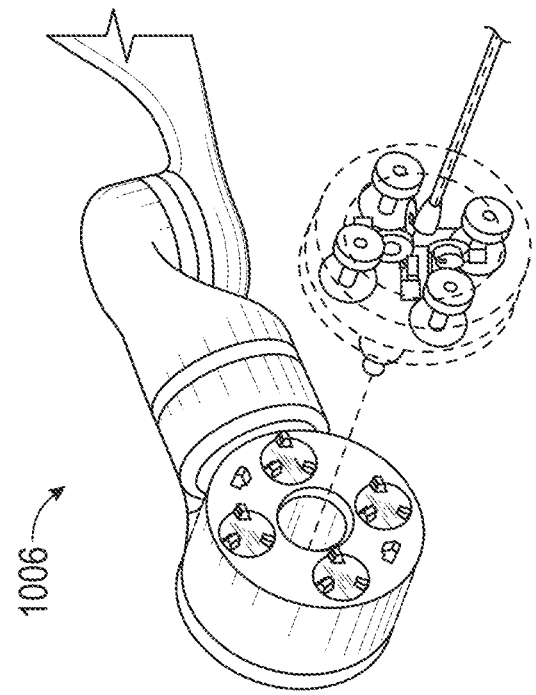
FIGS. 29A and 29B illustrate an example alignment of a dynamic model to a system model in accordance with aspects of this disclosure.
Figure 29A:
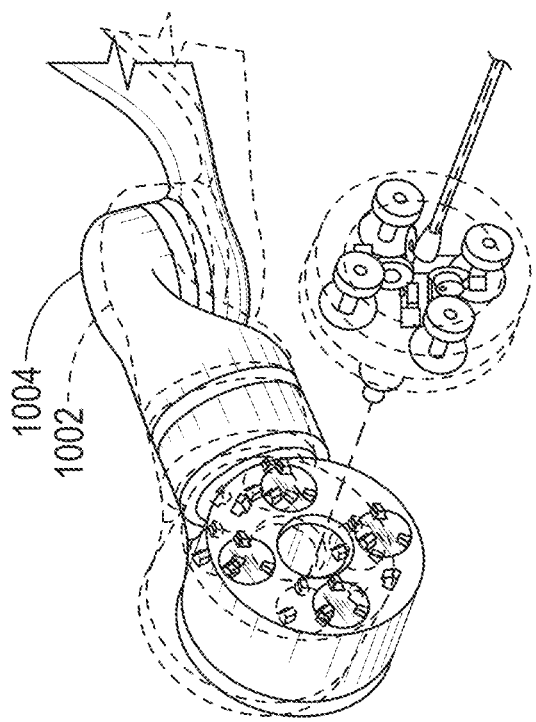

In certain implementations, the robotic medical system can include one or more sensors arranged in the operating room which can be used to generate a dynamic model of the robotic medical system. The sensors may be arranged such that at least a portion of the robotic medical system is within each of the sensor's field of view. Using these sensor(s) (e.g., such as the stereo cameras used to create the dynamic models 906 and 920 in FIGS. 28A and 28B), the robotic medical system can generate a dynamic model of the robotic system. The robotic medical system can align the dynamic model with the previously generated model of the robotic medical system (e.g., the model 500 of FIGS. 24A and 24B). The system can generate a transformation from the dynamic model into the system model using the alignment between the two models. FIGS. 29A and 29B illustrate an example alignment of a dynamic model 1002 to a system model 1004 in accordance with aspects of this disclosure.

In particular, FIG. 29A illustrates the dynamic model 1002 and the system model 1004 which are not aligned. The dynamic model 1002 can be generated using one or more sensors that provide a 3D point cloud (or mesh) representation that corresponds to the object(s) within the field of view of the sensor(s). For example, although the dynamic model 1002 and the system model 1004 may model substantially the same physical environment (e.g., a robotic arm, the operating room, etc.), the two models 1002 and 1004 may not be aligned within a shared coordinate system.

The system can align the dynamic model 1002 with the system model 1004 by finding a registration that transforms points in the dynamic model coordinate system to points in the system model coordinate system. For example, in certain implementations, the system can use a derivative of the Iterative Closest Point algorithm to align the dynamic model 1002 with the system model 1004. However, in other implementations, other alignment algorithms can be used. FIG. 29B illustrates a visualization of the two models being aligned 1006. After the alignment transformation is determined, the system can compare points in the dynamic model 1002 to points in the system model 1004. The system can identify any points from the dynamic model 1002 which are un-modeled in the system model 1004 as physical obstructions or objects which could potentially collide with the robotic arms. Thus, the system can use the alignment 1006 to map these objects into the system model 1004 and either avoid these object directly or update the location of both Pre-Model Objects or keep-out zones in the system model 1004.

E. Corrections to Improve Model Accuracy

Although a number of implementations for modeling objects in the context of collision avoidance are disclosed herein, there may be situations in which the generated object model is not sufficiently accurate. Adding a pre-modeled object (e.g., as described above in Section 2.A.) may depend on the user accurately placing the pre-modeled object in a location within the system model corresponding to the object's physical location. The advanced sensors used for pre-modeled objects (e.g., as described above in Section 2.B.) have inherent noise, for example, an encoder used for detecting the mounting angle might have error of +−0.2 degrees such that if a stirrup is 1 meter long then the error at the end point is 3 millimeters. A limit switch can have a similar problem in that the mounting bracket can be designed to have enough wiggle room to slide the accessory in and out, resulting in the activation range having +−1 mm of slop that will directly translate to the collision point. These errors can also compound and add up to an even larger error. Using keep-out zones (e.g., as described above in Section 2.C.) can depend on the user playing the objects or equipment accurately within the defined keep-out zone during use in order to remain completely inside this zone during the medical procedure. In addition, the use of advanced sensors (e.g., as described above in Section 2.D.) may have noise and can be occluded and not see parts of the object(s) the sensors are attempting to model. Thus, there may be sources of error and/or inaccuracy for any technique used to model objects such that the model may not sufficiently reflect the real-time state of the world for use in collision detection and avoidance.

The robotic medical system can maintain the safety of each robotic arm with respect to injury or damage during a procedure without reliance on object models, (e.g., by detecting collisions using force or torque sensors). However, these technique may involve stopping the procedure if a robotic arm collides with an object that is no longer accurately reflected by the corresponding object model. In order to prevent further collisions between the robotic arm(s) and the object, the system can automatically update the object model in response to a robotic arm detecting a collision with the object using a force or torque sensor. For example, the system can use the current position of the robotic arm at the time of the collision to expand the closest object model to include the collision position, thereby preventing future collisions at that point in space. In some embodiments, the system may wait for confirmation from the user (e.g., via a console) prior to updating the object model to include the collision location. Depending on the implementation, updates to the object model can involve moving the location of the object model with respect to the system model (e.g., for rigid object) and/or increasing the size of a keep-out zone to include the point of collision.

3. Implementing Systems and Terminology.

Implementations disclosed herein provide systems, methods and apparatus for collision avoidance using object models.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The functions for avoiding collisions in robotic arms using object models described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic medical system, comprising:
   a platform;
   one or more robotic arms coupled to the platform;
   a console configured to receive input commanding motion of the one or more robotic arms;
   a processor; and
   at least one computer-readable memory in communication with the processor and having stored thereon a model of the one or more robotic arms and computer-executable instructions to cause the processor to:
      control movement of the one or more robotic arms in a workspace based on the input received by the console,
      receive an indication of a plurality of objects being within reach of the one or more robotic arms, wherein the objects comprise a rigid object and a non-rigid object,
      update the model to include a representation of the objects in the workspace, wherein the representation of the rigid object is based on a pre-modeled representation stored on the computer-readable memory, and wherein the representation of the non-rigid object comprises one or more zones corresponding to the non-rigid object within the workspace based on a user input received at the console,
      receive a mounting location of the rigid object, wherein the rigid object is attached to the platform,
      detect a collision between the one or more robotic arms and the rigid object, and
      in response to the collision being detected, update the model by moving a location of the representation of the rigid object based on a position of the collision, wherein the position of the collision is based on the mounting location of the rigid object.

2. The system of claim 1, wherein the rigid object comprises one or more accessories that are attachable to the platform.

3. The system of claim 2, wherein the one or more accessories comprise at least one of the following: shoulder supports, foot supports, toboggans, leg boards, arm boards, fences, stirrups, poles, and tissue retractors.

4. The system of claim 1, wherein:
   the one or more zones comprise keep-out zones as geometric representations, and
   the computer-executable instructions further cause the processor to prevent movement of the one or more robotic arms into a region of the workspace corresponding to the keep-out zones.

5. The system of claim 1, wherein the non-rigid object comprises at least one of the following: IV bags, tubing, padding, objects associated with a patient including the patient, and objects associated with bedside staff including the bedside staff.

6. The system of claim 1, further comprising:
   one or more sensors positioned on the platform and configured to detect the objects,
   wherein the one or more sensors are configured to receive the indication of the objects being within reach of the one or more robotic arms.

7. The system of claim 6, wherein the platform comprises a bed including one or more adjustable arms supports, wherein the one or more sensors are positioned along the one or more adjustable arms supports.

8. The system of claim 1, further comprising:
   one or more sensors configured to detect the objects,
   wherein the one or more sensors comprise at least one of:
      a Lidar sensor, an electromagnetic sensor, and an image-based sensor.

9. The system of claim 1, wherein each of the one or more robotic arms includes a force sensor configured to detect the collision, wherein the position of the collision is based on a position of the one or more robotic arms in the workspace at a time of the collision.

10. The system of claim 1, wherein the computer-executable instructions further cause the processor to:
    receive a signal from one or more sensors positioned in the workspace,
    wherein the signal comprises the indication of the objects being within reach of the one or more robotic arms.

11. The system of claim 10, wherein the computer-executable instructions further cause the processor to:
    generate a dynamic model of the workspace based on the signal, and
    compare the dynamic model of the workspace to the model of the one or more robotic arms,
    wherein the model is further based on the comparison.

12. The system of claim 10, wherein the one or more sensors comprise at least one of: a stereo camera, a Lidar sensor, and an image based sensor.

13. The system of claim 1, wherein the pre-modeled representation is based on a 3D representation of the rigid object or a model using geometric forms.

14. The system of claim 1, wherein the computer-executable instructions further cause the processor to:
    receive a selection of an equipment type corresponding to the rigid object.

15. The system of claim 1, wherein the one or more zones comprise keep-out zones as geometric representations, wherein the computer-executable instructions further cause the processor to:

in response to the collision being detected, determine that the model does not accurately reflect a position of the at least one of the objects; and
increase a size of the keep-out zone to include the position of the collision.

16. A robotic medical system, comprising:
a platform;
one or more robotic arms coupled to the platform;
a console configured to receive input commanding motion of the one or more robotic arms;
a processor; and
at least one computer-readable memory in communication with the processor and having stored thereon a model of the one or more robotic arms, a database of pre-modeled objects, and computer-executable instructions to cause the processor to:
control movement of the one or more robotic arms based on the input received by the console,
receive an indication of a rigid object being within reach of the one or more robotic arms,
receive an indication of a non-rigid object being within reach of the one or more robotic arms,
receive a mounting location of the rigid object, wherein the rigid object is attached to the platform,
update the model to include a representation of the rigid object based on a pre-modeled representation stored on the computer-readable memory,
update the model to include a representation of the non-rigid object, wherein the representation of the non-rigid object comprises a zone corresponding to the non-rigid object within a workspace based on a user input received at the console,
detect a collision between the one or more robotic arms and the rigid object, and
in response to the collision being detected, update the model by moving a location of the representation of the rigid object based on a position of the collision, wherein the position of the collision is based on the mounting location of the rigid object.

17. The system of claim 16, further comprising:
one or more sensors positioned on the platform and configured to detect the rigid object,
wherein the one or more sensors are configured to receive the indication of the rigid object being within reach of the one or more robotic arms.

18. The system of claim 17, wherein the platform comprises a bed including one or more adjustable arms supports.

19. The system of claim 18, wherein the one or more sensors are positioned along the one or more adjustable arms supports.

20. The system of claim 19, wherein the one or more sensors comprise at least one of: a Lidar sensor, an electromagnetic sensor, and an image-based sensor.

21. The system of claim 16, wherein the computer-executable instructions further cause the processor to:
determine a location of a robotic arm that collided with the rigid object at a time of the collision, wherein the position of the collision is based on the location of the robotic arm.

22. A robotic medical system, comprising:
a platform;
one or more robotic arms coupled to the platform;
a console configured to receive user input;
a processor; and
at least one computer-readable memory in communication with the processor and having stored thereon a model of the one or more robotic arms and the platform and computer-executable instructions to cause the processor to:
receive an indication of one or more keep-out zones based on the user input received at the console, wherein the user input indicates a region of the model,
update the model to include the one or more keep-out zones,
detect a collision between the one or more robotic arms and an object, and
in response to the collision being detected, update a keep-out zone of the one or more keep-out zones by expanding the keep-out zone to include a position of the collision.

23. The system of claim 22, wherein, after the keep-out zone has been updated, the computer-executable instructions further cause the processor to:
prevent a second collision between the one or more robotic arms and the object based on the model.

24. The system of claim 22, wherein:
the one or more keep-out zones are pre-modeled, and
the computer-readable memory further has stored thereon a database of the one or more keep-out zones.

25. The system of claim 22, wherein the computer-executable instructions further cause the processor to receive a manually drawn boundary for the one or more keep-out zones via the console.

26. A robotic medical system, comprising:
a platform;
one or more robotic arms coupled to the platform;
one or more sensors positioned on the platform and configured to detect a plurality of objects in a workspace of the robotic arms;
a processor; and
at least one computer-readable memory in communication with the processor and having stored thereon a model of the one or more robotic arms and the platform and computer-executable instructions to cause the processor to:
receive an indication of the objects from the one or more sensors, wherein the objects comprise rigid objects and non-rigid objects,
update the model, based on the indication, to include a representation of the objects within the workspace, wherein the representation of the rigid objects is based on a pre-modeled representation stored on the computer-readable memory, and wherein the representation of the non-rigid objects comprises one or more zones corresponding to the non-rigid objects within the workspace based on a user input received at a console,
detect a collision between the one or more robotic arms and at least one of the objects, receive a confirmation via a user input to update the model based on the collision; and
in response to the confirmation being received, update the model by adjusting at least one of a location or a size of the representation of the at least one of the objects based on a position of the collision.

27. The system of claim 26, wherein the rigid objects do not move during a procedure.

28. The system of claim 26, wherein the model is updated by adjusting the location of the representation of the at least one of the objects.

29. The system of claim 26, wherein the model is updated by adjusting the size of the representation of the at least one of the objects when the at least one of the objects is a non-rigid object.

30. A robotic medical system, comprising:
a platform;
one or more robotic arms coupled to the platform;
a console configured to receive input commanding motion of the one or more robotic arms;
a processor; and
at least one computer-readable memory in communication with the processor and having stored thereon a model of the one or more robotic arms and computer-executable instructions to cause the processor to:
control movement of the one or more robotic arms in a workspace based on the input received by the console,
receive an indication of a plurality of objects being within reach of the one or more robotic arms, wherein the objects comprise a rigid object and a non-rigid object,
update the model to include a representation of the objects in the workspace, wherein the representation of the rigid object is based on a pre-modeled representation stored on the computer-readable memory, and wherein the representation of the non-rigid object comprises one or more zones corresponding to the non-rigid object within the workspace based on a user input received at the console, wherein the one or more zones comprise a keep-out zone as a geometric representation,
detect a collision between the one or more robotic arms and at least one of the objects,
in response to the collision being detected, update the model by moving a location of the representation of the at least one of the objects based on a position of the collision,
in response to the collision being detected, determine that the model does not accurately reflect a position of the at least one of the objects, and
increase a size of the keep-out zone to include the position of the collision.

* * * * *